United States Patent
Tanaka et al.

[11] Patent Number: 5,349,065
[45] Date of Patent: Sep. 20, 1994

[54] PHOTOCHROMIC COMPOUND

[75] Inventors: Takashi Tanaka, Shin-nanyo; Satoshi Imura; Kenji Tanaka, both of Tokuyama; Yasuji Kida, Kudamatsu, all of Japan

[73] Assignee: Tokuyama Soda Kabushiki Kaisha, Tokuyama, Japan

[21] Appl. No.: 977,882

[22] Filed: Nov. 17, 1992

Related U.S. Application Data

[62] Division of Ser. No. 806,324, Dec. 13, 1991, abandoned, which is a division of Ser. No. 491,157, Mar. 9, 1990, Pat. No. 5,106,998.

Foreign Application Priority Data

Jun. 5, 1989 [JP] Japan .................. 1-141206
Jun. 7, 1989 [JP] Japan .................. 1-143011

[51] Int. Cl.⁵ .................................. C07D 311/68
[52] U.S. Cl. .................................. 546/15; 546/89; 252/586
[58] Field of Search .................. 546/15, 89

[56] References Cited

U.S. PATENT DOCUMENTS 5,028,711  7/1991  Stenzel et al. .................. 546/15
5,061,813 10/1991  Atwal .................. 546/15

*Primary Examiner*—Johann Richter
*Assistant Examiner*—Catherine S. Kilby Scalzo
*Attorney, Agent, or Firm*—Sherman and Shalloway

[57] ABSTRACT

A compound represented by the following general formula (II):

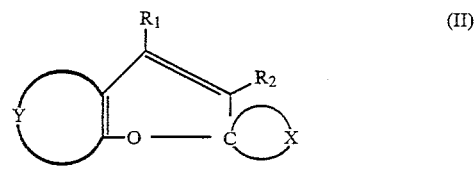

wherein $R_1$ and $R_2$, which may be the same or different, represent a hydrogen atom, an alkyl group having 1 to 20 carbon atoms, a phenyl group, a benzyl group, a phenethyl group, an alkylamine group having 1 to 4 carbon atoms, or a dialkylamino group having 2 to 8 carbon atoms, and

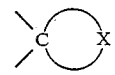

represents a nobornylidene group or bicyclo [3,3,1]9-nonylidene group which may have a substituent, and

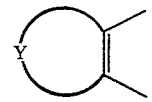

represents a pyridine, quinoline, pyrrole or benzothiophene group which may have a substituent.

10 Claims, 3 Drawing Sheets

PHOTOCHROMIC COMPOUND

This is a division of application Ser. No. 07/806,324 filed Dec. 13, 1991, which is a division of application Ser. No. 07/491,157, filed Mar. 9, 1990, now U.S. Pat. No. 5,106,998.

BACKGROUND OF THE INVENTION (1) Field of the Invention

The present invention relates to a novel compound having a photochromic action, a composition comprising this compound, and a use thereof. More particularly, the present invention relates to a novel compound which is colored from the colorless state under irradiation of an ultraviolet ray-containing light such as sunlight or a light of a mercury lamp, this change is reversible and the color fading speed is high, a composition comprising this novel compound and a use thereof.

(2) Description of the Related Art

The photochromism is the phenomenon which has attracted attention in these several years, and this phenomenon is a reversible phenomenon in which when a certain compound is irradiated with an ultraviolet ray-containing light such as sunlight or a light of a mercury lamp, the color of the compound is promptly changed and when the irradiation is stopped and the compound is placed in the dark place, the original color is manifested again. The compound having this property is called "photochromic compound", and various photochromic compound have been synthesized. However, a special common structure is not found among these compounds.

The specification of U.S. Pat. No. 4,826,977 discloses spiroadamantane compounds represented by the following formulae (A) and (B):

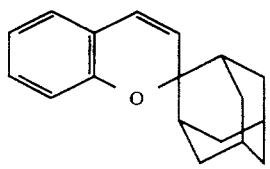

(A)

and

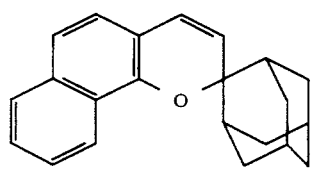

(B)

The compound (A) is poor in the practical utility because the coloration is caused only at temperatures lower than 10° C. The compound (B) shows a photochromic characteristic at temperatures close to normal temperature (10° to 40° C.), and it is known that the compound is changed to a yellow or orange color from the colorless state. However, in the spiroadamantane compound (B), the colored form is relatively stable and the color fading speed at the ambient temperature is not so high, presumably because of the presence of the bulky adamantylidene group. Therefore, when this compound is used for a photochromic lens, even by stopping irradiation with sunlight, a long time is required for restoring the lens to the colorless form from the colored form.

SUMMARY OF THE INVENTION

It is therefore a primary object of the present invention to provide a novel compound having a photochromic action.

Another object of the present invention is to provide a photochromic compound in which the color fading time required for restoring the compound to the colorless form from the colored form is short.

Still another object of the present invention is to provide a photochromic compound having a practical utility.

A further object of the present invention is to provide a polymer composition comprising a photochromic compound.

A still further object of the present invention is to provide a photochromic lens having a practical utility, As the result of research made by us, it was found that these objects can be attained by a photochromic compound described below.

More specifically, in accordance with the present invention, there is provided a compound represented by the following general formula (I):

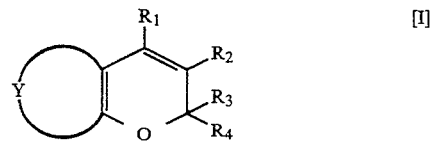

wherein $R_1$ and $R_2$, which may be the same or different, represent a hydrogen atom, an alkyl group, an aryl group, an aralkyl group or a substituted amino group, $R_3$ and $R_4$, which may be the same or different, represent an alkyl group, or $R_3$ and $R_4$ together form a norbornylidene group or bicyclo [3.3.1]9-nonylidene group which may have a substituent, and

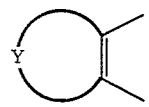

represents a divalent aromatic hydrocarbon group or divalent unsaturated heterocyclic group may have a substituent, with the proviso that when $R_3$ and $R_4$ represent an alkyl group,

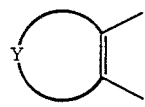

represents a bicyclic aromatic fused ring which is substituted with at least one substituent selected from the group consisting of a halogen atom, an alkyl group, an alkoxy group,

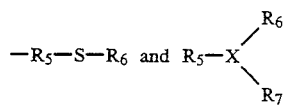

in which $R_5$ represents an alkylene group or $-(O-R_8)_n$ (in which $R_8$ represents an alkylene group and n is a positive integer), $R_6$ and $R_7$, which may be the same or different, represent an alkyl group, and X represents

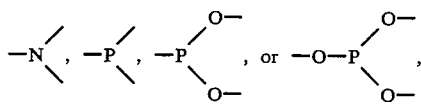

at least one of the substituents being an alkyl group having 6 to 20 carbon atoms, an alkoxy group having 6 to 20 carbon atoms,

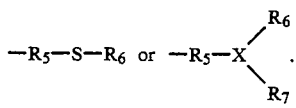

The foregoing and other objects and features of the present invention will become more apparent from the following description.

DETAILED DESCRIPTION OF THE PREFERRED EMBODIMENTS

Figure 1:
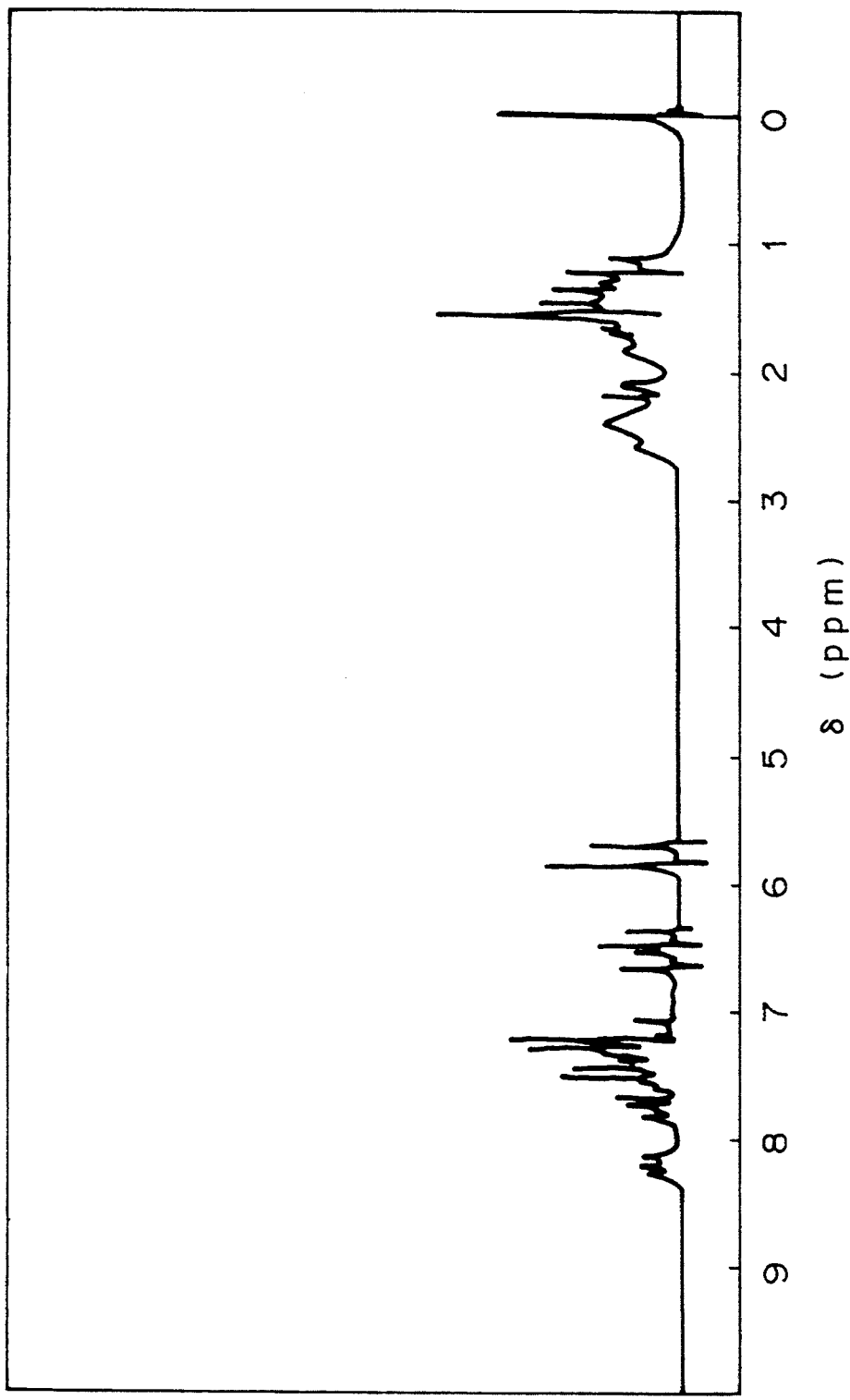
FIG. 1, 2 and 3 are $^1$H-nuclear magnetic resonance spectrum charts of compounds obtained in Example 1, 31 and 121, respectively.

In the above-mentioned general formula (I), $R_1$ and $R_2$, which may be the same or different, represent a hydrogen atom, an alkyl group, an aryl group, an aralkyl group or a substituted amino group.

As substituted amino group, there can be mentioned an alkylamino group, a dialkylamino group and a monovalent group derived from a 4- to 7-membered monocyclic saturated heterocyclic ring containing at least one nitrogen atom, or a nitrogen atom and an oxygen atom or sulfur atom. The 4- to 7-membered monocyclic saturated heterocyclic ring is represented by the following formula:

wherein $R_9$ represents an alkylene group having 3 to 6 carbon atoms, an oxyalkylene group having 3 to 6 carbon atoms, a thioalkylene group having 3 to 6 carbon atoms or an azoalkylene group having 3 to 6 carbon atoms.

As specific examples of $R_9$ in the above-mentioned formula, there can be mentioned alkylene group having 3 to 6 carbon atoms, such as a tetramethylene group and a pentamethylene group, oxyalkylene groups having 3 to 6 carbon atoms, such as $$-CH_2CHOCH_2-,\quad -CH_2OCH_2CH_2-,$$
$$\phantom{-CH_2C}|\phantom{HOCH_2-,\ -CH_2OCH_2CH_2,}$$
$$\phantom{-CH_2C}CH_2$$

$-CH_2CH_2OCH_2CH_2-$ and $-CH_2O(CH_2)_3-$, thioalkylene groups having 3 to 6 carbon atoms, such as $-CH_2SCH_2CH_2-$, $-CH_2S(CH_2)_3-$ or $-CH_2CH_2SCH_2CH_2-$, and azoalkylene groups having 3 to 6 carbon atoms, such as

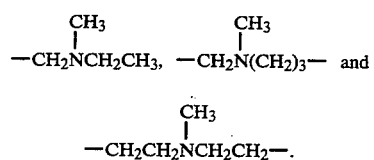

As specific examples of $R_1$ and $R_2$, there can be mentioned alkyl groups having 1 to 20 carbon atoms, such as a methyl group, an ethyl group, a propyl group, a butyl group, a pentyl group, an octyl group and a decyl group, aryl groups having 6 to 10 carbon atoms, such as a phenyl group, a tolyl group and a naphthyl group, and aralkyl groups having 7 to 10 carbon atoms, such as a benzyl group, a phenethyl group, a phenylpropyl group and a phenylbutyl group. As the substituted amino group, there can be mentioned alkylamino groups having 1 to 4 carbon atoms, such as a methylamino group or an ethylamino group, dialkylamino groups having 2 to 8 carbon atoms, such as a dimethylamino group and a diethylamino group, and monovalent groups derived from 4- to 7-membered mono-cyclic saturated heterocyclic rings containing at least one nitrogen atom, or a nitrogen atom and an oxygen atom or sulfur atom, such as a pyrrolidine ring, a piperidine ring, a piperazine ring, a morpholine ring and a thiazolidine ring.

Among them, a hydrogen atom, an alkyl group having 1 to 20 carbon atoms, an aryl group having 6 to 10 carbon atoms, an aralkyl group having 7 to 10 carbon atoms and a monovalent group derived from a 5- or 6-membered monocyclic saturated heterocyclic ring containing up to 2 nitrogen atoms, or one nitrogen atom and one oxygen or sulfur atom are preferable as $R_1$ and $R_2$.

The color fading speed of the compound of general formula (I) can be adjusted by selecting an appropriate group for $R_1$ or $R_2$. For example, when $R_1$ and $R_2$ represent an alkyl group, a high color fading speed can be obtained, probably because it is difficult for the compound to take the trans form where the compound is in the colored state, When $R_1$ is a substituted amino group, since the trans form where the compound is in the colored state is stabilized by the resonance, a high coloration density can be obtained, but the color fading speed is relatively low. Furthermore, the compound where both of $R_1$ and $R_2$ represent a hydrogen atom is characterized in that the compound is especially densely colored and the color fading speed is high.

In general formula (I), $R_3$ and $R_4$, which may be the same or different, represent an alkyl group, or they together form a norbornylidene group or bicyclo [3.3.1]9-nonylidene group which may have a substituent. As the alkyl group, there can be mentioned alkyl groups having 1 to 4 carbon atoms, such as a methyl group, an ethyl group and a butyl group. A compound in which both of $R_3$ and $R_4$ represent a methyl group is especially preferable.

In accordance with one preferred embodiment of the present invention, there is provided a compound represented by the following general formula (II):

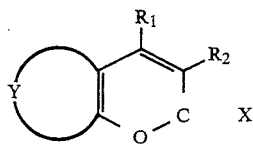

wherein

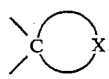

represents a norbornylidene group or bicyclo [3.3.1]9-nonylidene group which may have a substituent,

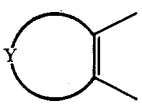

represents a divalent aromatic hydrocarbon group or divalent unsaturated heterocyclic group which may have a substituent, and $R_1$ and $R_2$, which may be the same or different, represent a hydrogen atom, an alkyl group, an aryl group, an aralkyl group or a substituted amino group.

The norbornylidene group is represented by the following formula:

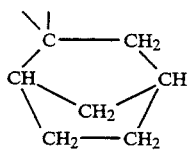

and the bicyclo [3.3.1]9-nonylidene group is represented by the following formula:

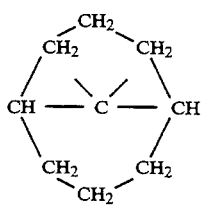

Hydrogen atoms of the norbornylidene group and bicyclo [3.3.1]9-nonylidene group represented by the above formulae can be substituted with substituents. The number of substituents can be 1 or larger, preferably 1 to 3. The kind, number and position of the substituents are appropriately selected according to the intended object and use. In the case where the bornylidene group or bicyclo [3.3.1]9-nonylidene group have a plurality of substituents, these substituents may be the same or different.

As the substituent of the norbornylidene group or bicyclo [3.3.1]9-nonylidene group, there can be mentioned halogen atoms such as fluorine, chlorine and bromine, a hydroxyl group, a cyano group, a nitro group, a carboxyl group, alkyl groups having 1 to 4 carbon atoms, such as a methyl group, an ethyl group, a propyl group and a butyl group, alkoxy groups having 1 to 4 carbon atoms, such as a methoxy group, an ethoxy group, a propoxy group and a butoxy group, halogenoalkyl groups having 1 to 4 carbon atoms, such as a trifluoromethyl group, aryl groups having 6 to 10 carbon atoms, such as a phenyl group, a tolyl group and a naphthyl group, aryloxy groups having 6 to 10 carbon atoms, such as a phenyloxy group, a tolyloxy group and a naphthyloxy group, aralkyl groups having 7 to 10 carbon atoms, such as a benzyl group, a phenethyl group and a phenylpropyl group, aralkoxy groups having 7 to 10 carbon atoms, such as a benzyloxy group, a phenethyloxy group and a phenylpropyloxy group, alkylamino groups having 1 to 4 carbon atoms, such as a methylamino group and an ethylamino group, dialkylamino groups having 2 to 8 carbon atoms, such as a dimethylamino group and a diethylamino group, and alkoxycarbonyl groups having 2 to 10 carbon atoms, such as a methoxycarbonyl group and an ethoxycarbonyl group.

As preferable examples of the substituent, there can be mentioned a halogen atom, a cyano group, an alkyl group having 1 to 4 carbon atoms, an alkoxy group having 1 to 4 carbon atoms, a halogenoalkyl group having 1 to 4 carbon atoms, an aryl group having 6 to 10 carbon atoms, an aralkyl group having 7 to 10 carbon atoms and a dialkyl-amino group having 2 to 8 carbon atoms.

In the above-mentioned general formula (I) in the present invention,

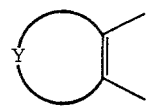

represents a divalent aromatic hydrocarbon group or divalent unsaturated heterocyclic group which may have a substituent. The aromatic hydrocarbon group has 6 to 18 carbon atoms, preferably 6 to 14 carbon atoms, and a divalent group derived from one benzene ring or a fused ring comprising 2 to 4 benzene rings is especially preferable. As examples of the ring constituting the aromatic hydrocarbon group, there can be mentioned a benzene ring, a naphthalene ring and a phenanthrene ring.

As the unsaturated heterocyclic group, there can be mentioned a 5- or 6-membered monocylic heterocyclic group containing one or two of nitrogen, oxygen and sulfur atoms, or a fused heterocyclic group formed by fusing a benzene ring to the above-mentioned monocyclic heterocyclic group. As the ring constituting the unsaturated heterocyclic group, there can be mentioned nitrogen-containing rings such as a pyridine ring, a quinoline ring and a pyrrole ring, oxygen-containing rings such as a furan ring and a benzofuran ring, and sulfur-containing rings such as a thiophene ring and a benzothiophene ring.

The aromatic hydrocarbon group or unsaturated hetero-cyclic group represented by

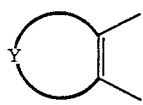

may have up to 5 substituents, preferably up to 3 substituents. As examples of the substituent, there can be mentioned halogen atoms such as fluorine, chlorine and bromine, a hydroxyl group, a cyano group, a nitro group, aryl groups having 6 to 10 carbon atoms, such as a phenyl group, a tolyl group and a naphthyl group, alkylamino groups having 1 to 4 carbon atoms, such as a methylamino group and an ethylamino group, dialkylamino groups having 2 to 8 carbon atoms, such as a dimethylamino group and a diethylamino group, halogenoalkyl groups having 1 to 4 carbon atoms, such as a trifluoromethyl group, monovalent groups derived from 5- or 6-membered monocyclic heterocyclic groups having one or two of sulfur, oxygen and nitrogen atoms, such as a thienyl group, a furyl group, a pyrrolyl group and a pyridyl group, alkyl groups having 1 to 20 carbon atoms, such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a pentadecyl group, an octadecyl group and an eicosyl group, alkoxy groups having 1 to 20 carbon atoms, such as a methoxy group, an ethoxy group, a propoxy group, a butoxy group, a penthloxy group, a hexyloxy group, a heptyloxy group, an octyloxy group, a nonyloxy group, a decyloxy group, an undecyloxy group, a dodecyloxy group, a pentadecyloxy group, an octadecyloxy group and an eicosyloxy group, and

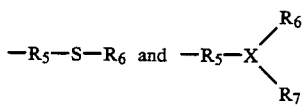

in which $R_5$ represents an alkylene group or $-(O-R_8)_n$ (in which $R_8$ represents an alkylene group and n is a positive integer), $R_6$ and $R_7$, which may be the same or different, represent an alkyl group, and X represents

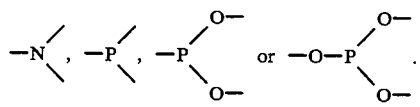

In the alkylene groups represented by $R_5$ and $R_8$ of the above substituents, the carbon number is not particularly critical, but in general, alkylene groups having 1 to 20 carbon atoms are selected. In view of the durability of the obtained compound as the photochromic material, alkylene groups having 6 to 20 carbon atoms are preferable. As specific examples of the alkylene group, there can be mentioned a methylene group, an ethylene group, a propylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a pentadecamethylene group, an octadecamethylene group and an eicosamethylene group. In $-(O-R_8)_n$ represented by $R_5$, n can be a positive integer, but it is generally preferred that n be selected so that the carbon number of the chain represented by $-(O-R_8)_n$ is 1 to 20, especially 6 to 20. Therefore, n is generally selected in the range of from 1 to 20.

In the alkyl groups represented by $R_6$ and $R_7$, the carbon number is not particularly critical, but in view of the color fading speed of the obtained compound as the photochromic material, it is preferred that the carbon number be 1 to 4.

In accordance with another preferred embodiment of the present invention, there is provided a compound represented by the following general formula (III):

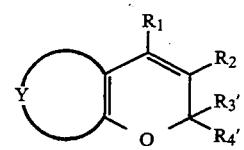

wherein $R_1$ and $R_2$, which may be the same or different, represent a hydrogen atom, an alkyl group, an aryl group, an aralkyl group or a substituted amino group, $R_3'$ and $R_4'$, which may be the same or different, represent an alkyl group,

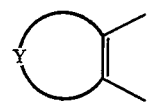

represents a bicyclic aromatic fused ring which is substituted with at least one substituent selected from the group consisting of a halogen atom, an alkyl group, an alkoxy group,

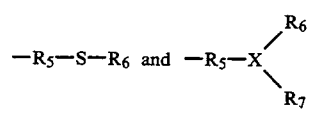

in which $R_5$ represents an alkylene group or $-(O-R_8)_n$ (in which $R_8$ represents an alkylene group and n is a positive integer), $R_6$ and $R_7$, which may be the same or different, represent an alkyl group and X represents

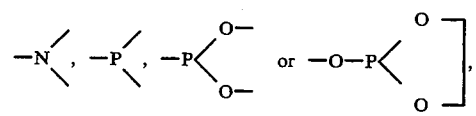

at least one of the substituents being an alkyl group having 6 to 20 carbon atoms, an alkoxy group having 6 to 20 carbon atoms,

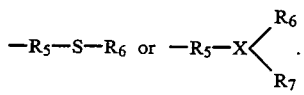

In the above-mentioned general formula (III),

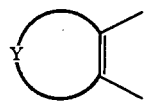

represents a bicyclic aromatic fused ring which is substituted with at least one substituents selected from the group consisting of the above-mentioned halogen atoms alkyl groups alkoxy groups,

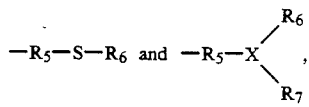

in which at least one of the substituents should be an alkyl group having 6 to 20 carbon atoms, an alkoxy group having 6 to 20 carbon atoms,

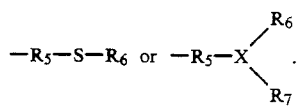

The bicyclic aromatic fused ring corresponds to a group formed by fusion of two 5- or 6-membered rings containing or not containing an oxygen atom, a sulfur atom or a nitrogen atom as the above-mentioned divalent aromatic hydrocarbon group or divalent unsaturated heterocyclic group.

In the case where $R_3$ and $R_4$ in the above-mentioned general formula (I) together form a norbornylidene group or bicyclo [3.3.1]9-nonylidene group, which may have a substituent,

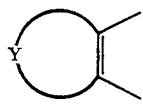

is preferably a divalent aromatic hydrocarbon group or divalent unsaturated heterocyclic group which may have at least one substituent selected from the group consisting of a halogen atom, a hydroxyl group, a cyano group, a nitro group, an alkyl group having 1 to 4 carbon atoms, an alkoxy group having 1 to 4 carbon atoms, an aryl group having 6 to 10 carbon atoms, a dialkyl amino group having 2 to 8 carbon atoms, a halogenoalkyl group having 1 to 4 carbon atoms and a monocyclic heterocyclic group.

Furthermore,

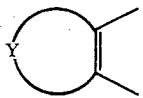

preferably represents a divalent group derived from a benzene ring or a fused ring comprising 2 to 4 benzene rings, or a divalent group derived from a 5-membered or 6-membered monocyclic heterocyclic ring containing one or two of oxygen, sulfur and nitrogen atoms or a fused ring formed by fusion of a benzene ring to this monocyclic heterocylic ring, which may have 1 to 3 substituents selected from the above-mentioned substituents.

Moreover,

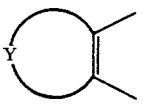

preferably represents a benzene ring, naphthalene ring, phenanthrene ring, pyridine ring, quinoline ring, pyrrole ring, furan ring, benzofuran ring, thiophene ring or benzothiophene ring which may have 1 to 3 substituents selected from the above-mentioned substituents.

In the case where both of $R_3$ and $R_4$ in the above-mentioned general formula (I) represent an alkyl group, as the bicyclic aromatic fused ring, there can be mentioned a naphthalene ring, a quinoline ring, an isoquinoline ring, an indole ring, an isoindole ring, a benzofuran ring and a benzothiophene ring. A compound in which an aromatic ring is fused at the 7,8-positions of the chromene is preferably used as the photochromic material because the coloration density is especially high.

In the case where the substituent of the bicyclic aromatic fused ring includes an alkyl group having 6 to 20 carbon atoms or an alkoxy group having 6 to 20 carbon atoms, the obtained compound is a photochromic material having an excellent durability. In contrast, in the case where the substituent of the bicyclic aromatic fused ring includes

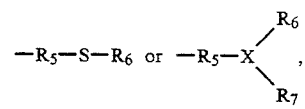

the obtained compound is a photochromic material having a high color fading speed.

The compound represented by the above-mentioned general formula (I) is a colorless or light yellow solid or viscous liquid at normal temperature under atmospheric pressure, and the compound can be identified, for example, by the following means (a) through (c).

(a) By measuring the proton nuclear magnetic resonance spectrum ($H_1$-NMR), the kind and number of protons present in the molecule can be known. Namely, a peak attributed to the aromatic proton appears in the vicinity of $\delta 7$ to 8.5 ppm and a broad peak attributed to the proton of the norbornylidene group or bicyclo [3.3.1]9-nonylidene group appears in the vicinity of $\delta 1.2$ to 2.5 ppm. In the case where both of $R_1$ and $R_2$ represent a hydrogen atom, a peak attributed to the proton of the alkene appears in the vicinity of $\delta 5.5$ to 7.0 ppm. By comparing the intensities of the $\delta$ peaks with one another, the numbers of protons of the respective binding groups can be known.

(b) The contents (% by weight) of carbon, hydrogen, nitrogen, sulfur and halogen can be determined by the elementary analysis. Furthermore, the content (% by weight) of oxygen can be calculated by subtracting the sum of the contents (% by weight) of the confirmed elements from 100. Accordingly, the composition of the product can be determined.

(c) By measuring the $^{13}C$-nuclear magnetic resonance spectrum, the kind of the carbon present in the molecule can be known. A peak attributed to the carbon of the norbornylidene group or bicyclo [3.3.1]9-nonylidene group appears in the vicinity of $\delta 27$ to 52 ppm, and in the case where both of $R_1$ and $R_2$ represents an alkyl group, a peak attributed to the carbon of the alkyl group appears in the vicinity of $\delta 15$ to 35 ppm and a peak attributed to the carbon of the aromatic hydrocarbon group or unsaturated heterocyclic group appears in the vicinity of $\delta 110$ to 150 ppm.

The process for the preparation of the compound of general formula (I) according to the present invention is not particularly critical. Typical processes preferably adopted will now be described.

More specifically, a compound of general formula (II) in which $R_1$ and $R_2$ represent a hydrogen atom or a substituted amino group, with the proviso that at least one of $R_1$ and $R_2$ is a substituted amino group, can be prepared by reacting a compound represented by the following general formula (IV):

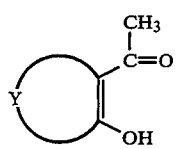  (IV)

wherein

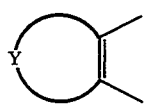

is as defined in general formula (II), with a compound represented by the following general formula (V):

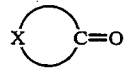

wherein

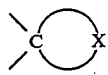

is as defined in general formula (II), in the presence of a primary amine or secondary amine.

The reaction between the compound of general formula (IV) and the compound of general formula (V) is carried out in the following manner. The reaction ratio between the two compounds can be selected from a broad range, but in general, this reaction ratio is in the range of from 1/10 to 10/1 (molar ratio). The reaction temperature is preferably 0° to 200° C. A polar nonprotonic solvent such as N-methylpyrrolidone, dimethylformamide or tetrahydrofuran is used as the reaction solvent. At this reaction, a condensing agent represented by a primary amine such as N-ethylamine or N-propylamine or a secondary amine such as pyrrolidine, piperidine or morpholine is used in an amount of 0.1 to 10 moles per mole of the compound of general formula (IV), and the reaction can be completed by removing water formed during the reaction. As the means for removing water, there can be mentioned a method in which water is removed from the reaction system by using a Dean-Stark apparatus, and a method in which a dehydrating agent such as calcium chloride, calcium oxide or zinc chloride is added into the reaction system and water formed in the reaction system is removed by this dehydrating agent. Any of these methods can be adopted.

By this reaction, a chromanone compound represented by the following general formula (VI):

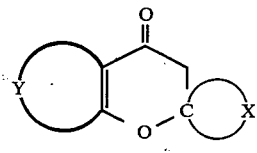  (VI)

wherein

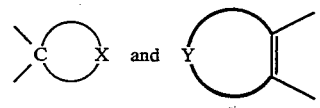

and are as defined in general formula (II), is obtained.

If the above reaction is further conducted, a compound of general formula (II) in which at least one of $R_1$ and $R_2$ is a substituted amino group, that is, a compound represented by the following general formula (VII):

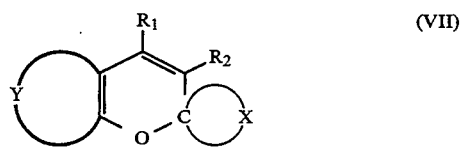  (VII)

wherein

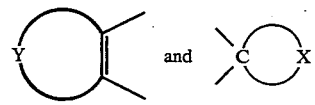

are as defined in general formula (II), and $R_1$ and $R_2$, which may be the same or different, represent a hydrogen atom or a substituted amino group, with the proviso that at least one $R_1$ and $R_2$ is a substituted amino group, is obtained.

A compound of the above-mentioned general formula (II) in which each of $R_1$ and $R_2$ is a hydrogen atom can be prepared in the following manner. Namely, a chromanone compound of general formula (VI) is reacted with a reducing agent such as sodium boron hydride or lithium aluminum hydride to form a chromanol compound represented by the following formula:

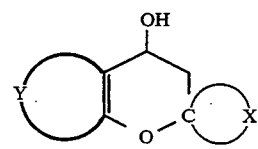

wherein

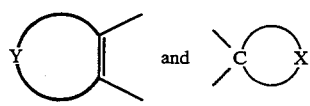

are as defined in general formula (II), and then, this compound is dehydrated with a dehydrating agent such as anhydrous copper sulfate to obtain a compound represented by the following general formula (VIII):

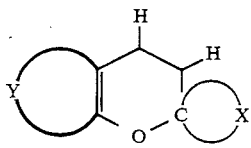

(VIII)

wherein

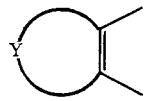 and 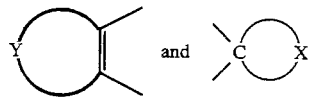

are as defined in general formula (II).

A compound of general formula (II) in which $R_1$ is an alkyl group, aralkyl group or aryl group can be prepared in the following manner. Namely, a chromanone compound represented by the above-mentioned formula (VI) is reacted with an organic metal compound such as an alkyl magnesium halide or an alkyl lithium halide to form a chromanol compound represented by the following general formula (IX):

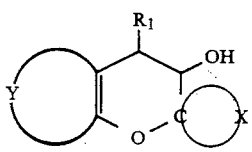

(IX)

wherein

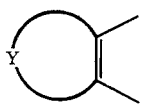 and 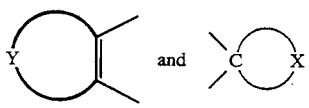

are as defined in general formula (II), and $R_1$ represents an alkyl group, an aralkyl group or an aryl group, and then, this chromanol compound is dehydrated with a dehydrating agent such as anhydrous copper sulfate to obtain a compound represented by the following general formula (X):

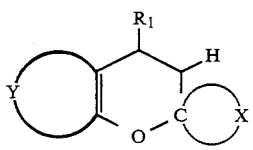

(X)

wherein

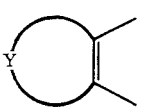 and 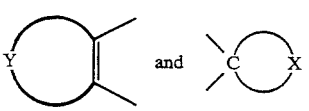

are as defined in general formula (II), and $R_1$ represents an alkyl group, an aralkyl group or an aryl group.

A compound of general formula (II) where $R_2$ represents an alkyl group, an aralkyl group or an aryl group can be prepared in the following manner. Namely, a compound represented by general formula (VII) is reacted with an alkyl halide, an aryl halide or an aralkyl halide to obtain a chromanone compound represented by the following general formula (XI):

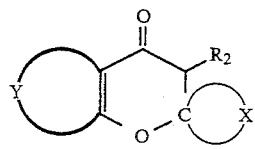

(XI)

wherein

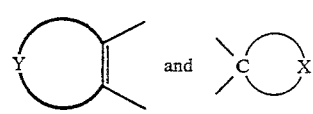 and 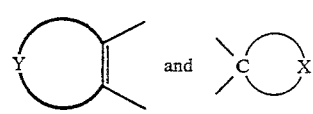

are as defined in general formula (II), and $R_2$ represents an alkyl group, an aralkyl group or an aryl group, and then, this chromanone compound is reduced in the same manner as described above and dehydrated with a dehydrating agent to obtain a compound represented by the following general formula (XII):

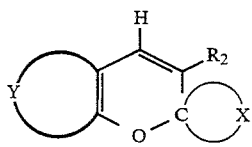

(XII)

wherein

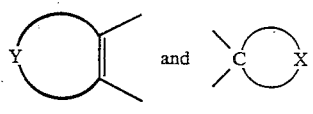 and 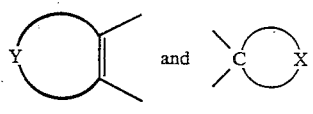

are as defined in general formula (II), and $R_2$ represents an alkyl group, an aralkyl group or an aryl group.

Furthermore, if a chromanone compound of general formula (XI) is reacted with an organic metal compound such as an alkyl magnesium halide in the same manner as described above and is then dehydrated with a dehydrating agent, a compound represented by the following general formula (II'):

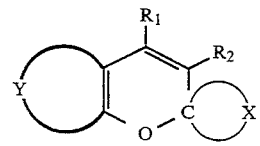

(II')

wherein

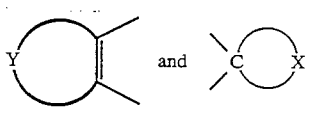 and 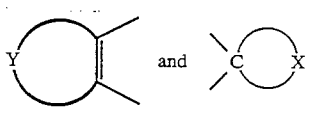

are as defined in general formula (II), and $R_1$ and $R_2$, which may be the same or different, represent an alkyl group, an aralkyl group or an aryl group, is obtained.

The process for the preparation of the compound represented by the above-mentioned general formula (III) will now be described.

At first, a compound represented by the following general formula (IV):

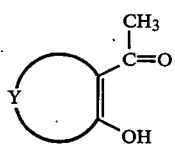 (IV)

wherein

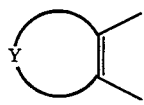

is as defined in general formula (III), is reacted with a ketone represented by the following general formula (XIII):

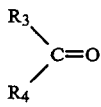 (XIII)

wherein $R_3$ and $R_4$ are as defined in general formula (III), in the presence of a condensing agent to obtain a compound represented by the following general formula (XIV):

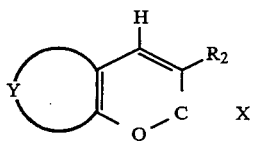 (XII)

wherein

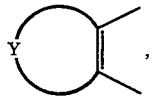

$R_3$ and $R_4$ are as defined in general formula (III).

The reaction between the compound of general formula (IV) and the compound of general formula (XIII) is carried out in the following manner. The reaction ratio between the two compounds can be selected in a broad range, but in general, the reaction ratio is selected in the range of from 1/10 to 10/1 (molar ratio). It is generally preferred that the reaction temperature be 0° to 200° C. A polar nonprotonic solvent such as N-methylpyrrolidone, dimethylformamide or tetrahydrofuran is used as the reaction solvent. At this reaction, a condensing agent represented by a secondary amine such as pyrrolidine, piperidine or morpholine is used in an amount of 0.1 to 10 moles per mole of the compound represented by general formula (IV), and the reaction is completed by removing water formed by the reaction. As the means for removing water, there can be mentioned a method in which water is removed from the reaction system by using a Dean-Stark apparatus, and a method in which a dehydrating agent such as calcium chloride, calcium oxide or zinc chloride is added to the reaction system and water formed in the reaction system is removed by this dehydrating agent. Any of these methods can be adopted.

A compound represented by the above-mentioned general formula (III) can be obtained by reacting the above-mentioned chromanone compound with a reducing agent such as sodium boron hydride or lithium aluminum hydride to form a chromanol compound represented by the following general formula (XV):

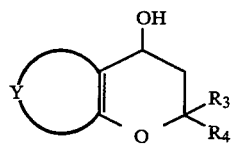 (XV)

wherein

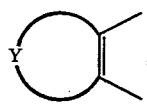

$R_3$ and $R_4$ are as defined in general formula (III), and dehydrating the chromanol compound with a dehydrating agent such as anhydrous copper sulfate.

As another synthesis process, there can be mentioned a process in which a compound represented by the following general formula (XVI):

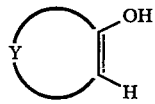 (XVI)

wherein

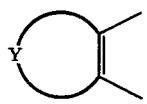

is as defined in general formula (III), is reacted with 3-methyl-2-butenal [OHCCH=C(CH$_3$)$_2$] in the presence of a condensing agent to form a compound represented by the above-mentioned general formula (III) in which both of $R_3$ and $R_4$ represent a methyl group.

The reaction between the compound of general formula (XVI) and 3-methyl-2-butenal is carried out in the following manner. The reaction ratio between the two compounds can be selected in a broad range, but in general, the reaction ratio is selected in the range of from 1/10 to 10/1 (molar ratio). It is generally preferred that the reaction temperature be 0° to 200° C. A polar nonprotonic solvent such as N-methylpyrrolidone, dimethylformamide, tetrahydrofuran, chloroform or carbon tetrachloride is used as the reaction solvent. At this reaction, a metal compound, for example, a tetravalent titanium compound such as titanium (IV) ethoxide, titanium (IV) isopropoxide or titanium (IV) chloride, a magnesium compound such as diethyl magnesium, dipropyl magnesium or magnesium chloride, an aluminum compound such as aluminum methoxide, aluminum ethoxide, aluminum isopropoxide or aluminum chloride, or a tin (IV) compound such as tin (IV) chloride is used as the condensing agent in an amount of 0.1 to 10 moles per mole of the compound of general formula (XVI).

The compound of the above-mentioned general formula (I) according to the present invention is well soluble in ordinary organic solvents such as toluene, chloroform and tetrahydrofuran. If the compound of general formula (I) is dissolved in such an organic solvent, the solution is generally colorless and transparent. When the solution is irradiated with sunlight or ultraviolet rays, the solution is promptly colored. If the solution is insulated from the light, the solution is promptly restored to the original colorless state. Thus, the compound of general formula (I) shows a good reversible photochromic action. This photochromic action of the compound of general formula (I) is also caused in a polymeric solid matrix. Any of polymers in which the compound of general formula (I) according to the present invention is uniformly dispersed can be used as the polymer constituting the polymeric matrix. From the optical viewpoint, there are preferably used polymethyl acrylate, polyethyl acrylate, polymethyl methacrylate, polyethyl methacrylate, polystyrene, polyacrylonitrile, polyvinyl alcohol, polyacrylamide, poly(2-hydroxyethyl methacrylate), polydimethylsiloxane, polycarbonate, poly(allyl diglycol carbonate), and copolymers of monomers constituting these polymers and copolymers of these monomers with other monomers.

The compound of general formula (I) according to the present invention is dispersed in a polymer as mentioned above in an amount of 0.001 to 70 parts by weight, preferably 0.005 to 30 parts by weight, per 100 parts by weight of the polymer.

The compound of the present invention is superior to the conventional spiroadamantane compounds especially in the color fading speed.

Accordingly, the compound of the present invention can be widely used as the photochromic compound. For example, the compound of the present invention can be used as various recording materials, for example, various memory materials, copying materials, printing photosensitive materials, cathode ray tube recording materials, laser photosensitive materials and holographic photosensitive materials instead of the conventional silver salt photosensitive materials. Furthermore, the photochromic material comprising the compound of the present invention can be used as a photochromic lens material, an optical filter material, a display material, an actinometer material and a decorative material. For example, when the material is used for a photochromic lens, any method can be used without any particular limitation, so far as a uniform dimming performance is obtained. For example, there can be adopted in which a homogeneous dispersion of the compound of the present invention in a polymer film is sandwiched in a lens, and a method in which the compound of the present invention is dissolved in, for example, a silicone oil, the surface of a lens is impregnated with the solution at 150° to 200° C. over a period of 10 to 60 minutes and the impregnated surface is covered with a hardenable substance to form a photochromic lens. Furthermore, there can be considered a method in which the above-mentioned polymer film is coated on the surface of a lens and the surface is covered with a hardenable substance to form a photochromic lens.

A photochromic material which is densely colored at a temperature close to normal temperature under irradiation with sunlight is preferably used for the photochromic lens. A compound of general formula (I) in which

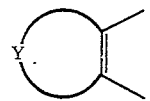

represents a divalent group derived from a naphthalene ring, a phenanthrene ring, a pyridine ring or a quinoline ring is especially preferably used for the photochromic lens.

The compound of general formula (I) according to the present invention generally shows a colorless state stable in a polymeric solid matrix substantially irrespectively of the kind of the matrix, but if the compound is irradiated with ultraviolet rays, the compound is immediately colored, and when the irradiation is stopped, the compound is rendered colorless at a high color fading speed in the order of seconds, and the compound of the present invention is characterized in that this coloration-fading can be repeated with a good durability.

The present invention will now be described in detail with reference to the following examples that by no means limit the scope of the invention.

EXAMPLE 1

A solution was prepared by dissolving 10 g (0.054 mole) of 1-hydroxy-2-acetonaphthone, 6.6 g (0.06 mole) of norcamphor and 8 g (0.113 mole) of pyrrolidine in 300 cc of toluene. The solution was boiled for 10 hours and water was separated. After termination of the reaction, toluene was removed under reduced pressure, and the remaining chromanone compound was crystallized with acetone. Then, the chromanone compound was dissolved in 200 cc of methanol, and sodium boron hydride was gradually added to the solution to form a chromanol compound. Then, 7.47 g of the chromanol compound was heated at 150° to 160° C. together with 4.5 g of anhydrous copper sulfate in a carbon dioxide current for 10 minutes and the obtained viscous liquid was purified by the chromatography on silica gel to obtain 6.3 g of a chromene compound of the following formula:

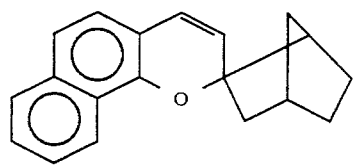

(1)

The elementary analysis values of the obtained compound were 86.93% for C, 6.89% for H and 6.18% for 0, O. which were well in agreement with the theoretical values of $C_{19}H_{18}O$, that is, 87.02% for C, 6.87% for H and 6.12% for O. When the proton nuclear magnetic resonance spectrum (FIG. 1) was measured, it was found that a peak of 6H attributed to the proton of the naphthalene ring appeared in the vicinity of $\delta 7.2$ to 8.3 ppm, a peak of 2H attributed to the proton of the alkene appeared in the vicinity of $\delta 5.6$ to 6.7 ppm and a broad peak of 10H attributed to the proton of the norbornylidene group appeared in the vicinity of $\delta 1.2$ to 2.5 ppm. When the $^{13}C$-nuclear magnetic resonance spectrum was measured, it was found that a peak attributed to the carbon of the norbornylidene group appeared in the vicinity of $\delta 27$ to 52 ppm, a peak attributed to the carbon of the naphthalene ring appeared in the vicinity of δ110 to 160 ppm and a peak attributed to the carbon of the alkene appeared in the vicinity of δ80 to 110 ppm. From the foregoing results, it was confirmed that the isolated product is the compound represented by the above-mentioned structural formula (1).

EXAMPLE 2

A solution was prepared by dissolving 10 g (0.054 mole) of 1-acetyl-2-naphthol, 6.6 g (0.06 mole) of norcamphor and 8.7 g (0.10 mole) of morpholine in 300 cc of toluene, and the solution was boiled for 5 hours and water was separated. After termination of the reaction toluene was removed under reduced pressure, and the remaining chromanone compound was recrystallized from acetone, and the chromanon compound was dissolved in 200 cc of methanol and lithium aluminum hydride was added to the solution to form a chromanol compound. Then, 6.49 g of this chromanol compound was heated at 170° to 180° C. together with anhydrous copper sulfate in a carbon dioxide current for 10 minutes and the obtained brown viscous liquid was purified by the chromatography on silica gel to obtain 5.1 g of a chromene compound represented by the following formula:

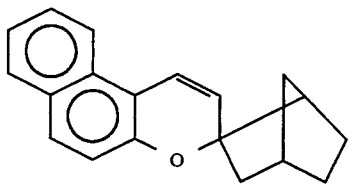
(2)

The elementary analysis values of this compound were 86.86% for C, 6.91% for H and 6.22% for O, which were well in agreement with the theoretical values of $C_{19}H_{18}O$, that is, 87.02% for C, 6.87% for H and 6.12% for O. When the proton nuclear magnetic resonance spectrum was measured, it was found that a peak of 6H attributed to the proton of the naphthalene ring appeared in the vicinity of δ7.2 to 8.3 ppm, a peak of 2H attributed to the proton of the alkene appeared in the vicinity of δ6.0 to 7.0 ppm and a broad peak of 10H attributed to the proton of the norbornylidene group appeared in the vicinity of δ1.2 to 2.5 ppm. When the $^{13}C$-nuclear magnetic resonance spectrum was measured, it was found that a peak attributed to the carbon of the norbornylidene group appeared in the vicinity of δ27 to 52 ppm, a peak attributed to the carbon atom of the naphthalene ring appeared in the vicinity of δ110 to 160 ppm and a peak attributed to the carbon atom of the alkene appeared in the vicinity of δ90 to 110 ppm. From the foregoing results, it was confirmed that the isolated product is the compound represented by the above-mentioned structural formula (2).

EXAMPLE 3

In 50 cc of anhydrous ether was dissolved 2.78 g (0.01 mole) of the chromanone compound obtained in Example 2, represented by the following formula:

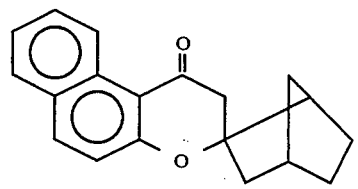

and the solution was cooled to 0° C. and 0.012 mole of Grignard reagent $CH_3MgI$ newly prepared in 50 cc of anhydrous ether was dropped into the solution over a period of about 1 hour. After termination of the dropwise addition, the mixture was stirred at room temperature for 2 hours and was gradually poured into cold water to extract the product with ether. The ether extract was dried on magnesium sulfate and ether was removed under reduced pressure to form a chromanol compound from the chromanon compound. Then, the obtained chromanol compound was heated at 200° C. together with anhydrous copper sulfate in a carbon dioxide current for about 10 minutes, and the obtained brown viscous liquid was purified by the chromatography on silica gel to obtain 2.24 g of a chromene compound represented by the following formula:

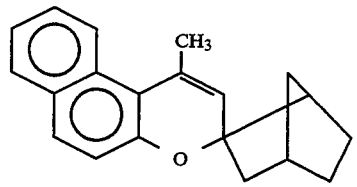
(3)

The elementary analysis, proton nuclear magnetic resonance measurement and $^{13}C$-nuclear magnetic resonance spectrum measurement were carried out in the same manner as described in Example 2. From the obtained results, it was confirmed that the obtained compound is the compound represented by the above-mentioned structural formula (3). The elementary analysis values of this compound and the theoretical values calculated from the composition of the compound (3) are shown in Table 2.

EXAMPLE 4

In 300 cc of toluene were dissolved 10 g (0.054 mole) of 1-acetyl-2-naphthol, 6.6 g (0.06 mole) of norcamphor and 8.7 g (0.10 mole) of morpholine, and solution was boiled for 15 hours and water was separated. After termination of the reaction, toluene was removed under reduced pressure and the remaining product was recrystallized from acetone to obtain 7.53 g of a compound represented by the following formula:

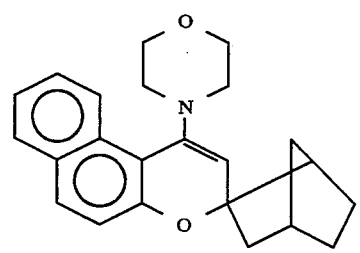

Then, 7.53 g of this compound was dissolved in 100 cc of methanol and reacted with methyl iodide to obtain 6.95 g of a chromanone compound represented by the following formula:

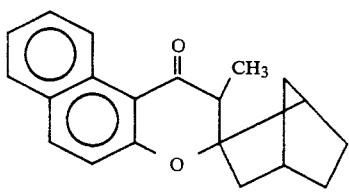

Then, the so-obtained chromanone compound was converted to a chromanol compound in the same manner as described in Example 2, and the dehydration reaction was carried out. Then, the separation and purification were carried out to obtain a 5.84 g of a chromene compound represented by the following formula:

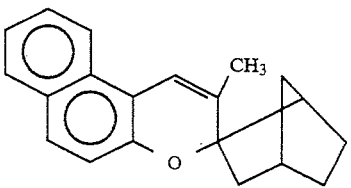

(4)

The elementary analysis, proton nuclear magnetic resonance measurement and $^{13}$C-nuclear magnetic resonance spectrum measurement were carried out in the same manner as described in Example 2. From the obtained results, it was confirmed that the obtained compound is the compound represented by the above-mentioned structural formula (4). The elementary analysis values of the obtained compound and the theoretical values calculated from the composition of the compound (4) are shown in Table 2.

EXAMPLES 5 THROUGH 30

Various chromene compounds were prepared from starting compounds shown in Table 1 in the same manner as described in Examples 1 through 4. Namely, in Table 1, in Examples 5 through 9, the reaction was carried out in the same manner as described in Example 4, and in Examples 10 through 25, the reaction was carried out in the same manner as described in Example 1. In Examples 26 through 30, the reaction was carried out in the same manner as described in Example 3 or 4.

The structures of the obtained compounds were analyzed by the same structure-confirming means as adopted in Example 1. It was confirmed that the obtained compounds are compounds represented by structural formula shown in Table 1.

TABLE 1

| Example No. | Starting Compounds | Condensing agent | Products | Yield (%) |
|---|---|---|---|---|
| 5 | 2'-hydroxyacetophenone | pyrrolidine | (spiro bicyclic chromene with pyrrolidine enamine) | 41 |
| 6 | 2'-hydroxy-4'-ethyl-6'-methoxyacetophenone | morpholine | (spiro bicyclic chromene with morpholine enamine, H₃CO and C₂H₅ substituents) | 38 |
| 7 | 1-acetyl-2-hydroxynaphthalene | diethylamine | (N(CH₃)₂-substituted bicyclic naphthochromene with N(C₂H₅)₂ enamine) | 46 |
| 8 | 1-acetyl-2-hydroxy-8-chloronaphthalene | thiomorpholine | (OCH₃-substituted bicyclic naphthochromene with thiomorpholine enamine, Cl substituent) | 40 |

TABLE 1-continued

| | | | | |
|---|---|---|---|---|
| 9 | (4-hydroxyquinoline-3-carbonyl structure) | (bicyclic ketone) | (N-methylpiperazine) | 36 |
| 10 | | | | 43 |
| 11 | | | | 36 |
| 12 | | | | 39 |

TABLE 1-continued
| | | | |
|---|---|---|---|
| 13 | 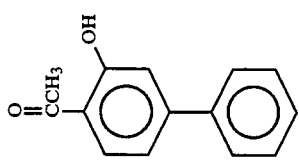 | 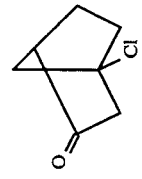 | " | 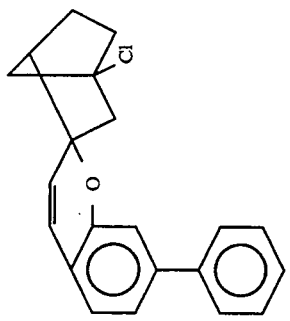 | 29 |
| 14 | | | pyrrolidine | 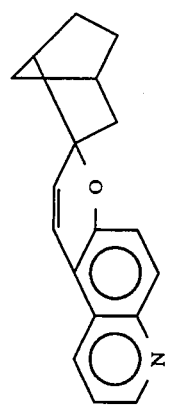 | 40 |
| 15 | | 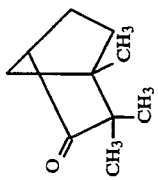 | pyrrolidine | 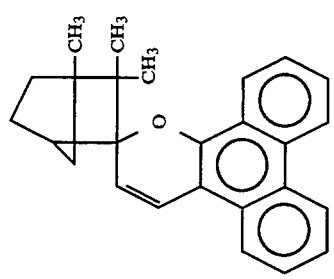 | 39 |

TABLE 1-continued

| | | | |
|---|---|---|---|
| 16 | (naphthol with OH, CCH₃=O, H₅C₂O, NO₂ substituents) | (bicyclic ketone with CH₃, CH₃, CH₃ groups) | 30 (chromene structure with NO₂, OC₂H₅, CH₃ groups) |
| 17 | (naphthol with OH, CCH₃=O, C₅H₉, CF₃ substituents) | (bicyclic ketone with CH₃, CH₃, CH₃ groups) | 42 (chromene structure with CF₃, C₅H₉, CH₃ groups) |
| 18 | (naphthol with OH, CCH₃=O, phenyl substituents) | (bicyclic ketone with phenyl group) | 40 pyrrolidine (chromene structure with phenyl groups) |

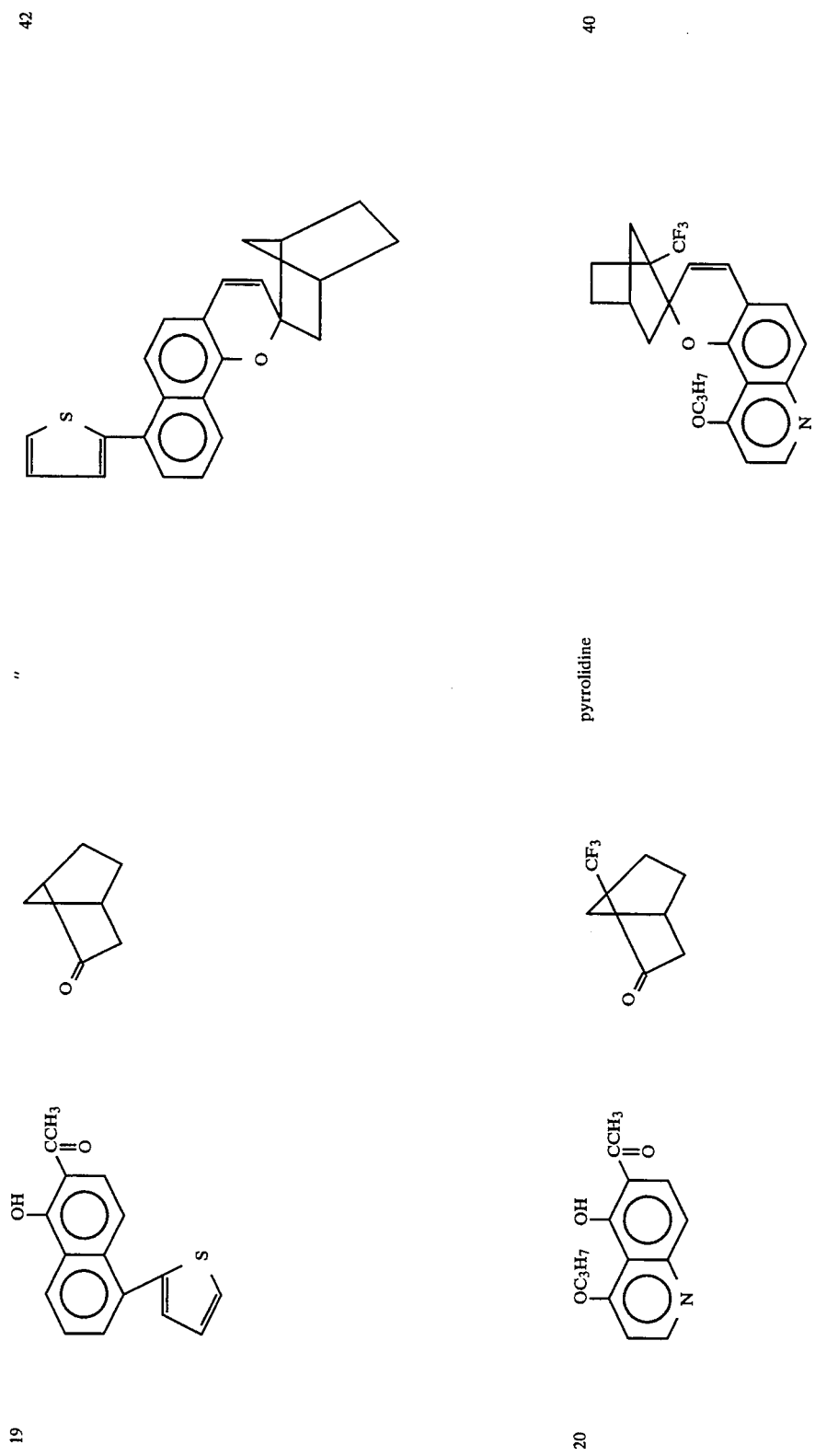

TABLE 1-continued

| | | | |
|---|---|---|---|
| 21 | (structure) | (structure) | 43 |
| 22 | (structure) | (structure) | 41 |
| 23 | (structure) | (structure) | 36, pyrrolidine |

TABLE 1-continued

| Example No. | Starting Compounds | | Products | Yield (%) |
|---|---|---|---|---|
| 24 | [structure: 2-acetyl-3-hydroxy benzothiophene] | [structure: 1-ethoxy-4-ethyl bicyclic ketone] | [structure: benzothiopyran fused product with OC₂H₅ and C₂H₅] | 34 |
| 25 | [structure: 1-methyl-3-acetyl-2-hydroxy pyrrole] | " | [structure: N-methyl pyrano-pyrrole spiro product] | 38 |
| 26 | [structure: quinoline-fused chromanone with spiro cyclopentane] | [structure: C₆H₅CH₂MgBr] | [structure: quinoline chromene with CH₂-phenyl substituent] | 62 |
| 27 | [structure: 8-cyano chromanone with spiro cyclopentane] | CH₃CH₂CH₂CH₂MgBr | [structure: 8-cyano chromene with (CH₂)₃CH₃ substituent] | 65 |

TABLE 1-continued

| | | | |
|---|---|---|---|
| 28 | (ketone structure) | PhMgBr | (phenyl-substituted pyrano-pyridine) | 70 |
| 29 | (pyrrolidinyl naphthopyran) | CH₃CH₂CH₂Br | (propyl-substituted naphthopyran) | 64 |
| 30 | (pyrrolidinyl naphthopyran) | PhCH₂CH₂Br | (phenethyl-substituted naphthopyran) | 64 |

TABLE 2

| Compound No. | Elementary Analysis Values (%) | | | | | Theoretical Values (%) | | | | |
|---|---|---|---|---|---|---|---|---|---|---|
| | C | H | N | O | others | C | H | N | O | others |
| 1 | 86.93 | 6.89 | — | 6.18 | — | 87.02 | 6.87 | — | 6.12 | — |
| 2 | 86.86 | 6.91 | — | 6.22 | — | 87.02 | 6.87 | — | 6.12 | — |
| 3 | 86.86 | 7.27 | — | 5.87 | — | 86.96 | 7.25 | — | 5.80 | — |
| 4 | 86.90 | 7.29 | — | 5.81 | — | 86.96 | 7.25 | — | 5.80 | — |
| 5 | 81.10 | 8.21 | 5.01 | 5.68 | — | 81.14 | 8.19 | 4.98 | 5.69 | — |
| 6 | 77.90 | 8.49 | 4.16 | 9.45 | — | 77.88 | 8.55 | 4.13 | 9.44 | — |
| 7 | 79.83 | 8.52 | 7.42 | 4.23 | — | 79.79 | 8.51 | 7.45 | 4.26 | — |
| 8 | 66.69 | 5.83 | 3.30 | 7.69 | S 7.76 Cl 8.73 | 66.75 | 5.80 | 3.38 | 7.74 | S 7.74 Cl 8.59 |
| 9 | 76.21 | 7.56 | 11.69 | 4.54 | — | 76.45 | 7.48 | 11.63 | 4.43 | — |
| 10 | 80.20 | 8.19 | 5.52 | 6.09 | — | 80.00 | 8.24 | 5.49 | 6.27 | — |
| 11 | 80.90 | 6.38 | 5.94 | 6.78 | — | 81.01 | 6.33 | 5.91 | 6.75 | — |
| 12 | 88.04 | 7.83 | — | 4.13 | — | 87.96 | 7.85 | — | 4.19 | — |
| 13 | 78.21 | 5.84 | — | 4.89 | Cl 11.06 | 78.14 | 5.89 | — | 4.96 | Cl 11.00 |
| 14 | 82.11 | 6.54 | 5.30 | 6.05 | — | 82.13 | 6.46 | 5.32 | 6.08 | — |
| 15 | 88.10 | 7.38 | — | 4.52 | — | 88.14 | 7.34 | — | 4.52 | — |
| 16 | 73.35 | 6.80 | 3.52 | 16.33 | — | 73.28 | 6.87 | 3.56 | 16.28 | — |
| 17 | 76.41 | 7.01 | — | 3.70 | F 12.88 | 76.36 | 7.05 | — | 3.64 | F 12.95 |
| 18 | 89.80 | 6.29 | — | 3.91 | — | 89.86 | 6.28 | — | 3.86 | — |
| 19 | 80.19 | 5.84 | — | 4.61 | S 9.36 | 80.23 | 5.81 | — | 4.65 | S 9.30 |
| 20 | 67.81 | 5.72 | 3.64 | 8.17 | F 14.66 | 67.87 | 5.66 | 3.60 | 8.23 | F 14.65 |
| 21 | 81.43 | 5.39 | 3.92 | 9.26 | — | 81.59 | 5.38 | 3.97 | 9.07 | — |
| 22 | 56.61 | 4.69 | — | 9.47 | F 5.64 Br 23.59 | 56.65 | 4.72 | — | 9.44 | F 5.61 Br 23.57 |
| 23 | 81.32 | 7.56 | 3.42 | 7.70 | — | 81.36 | 7.51 | 3.39 | 7.75 | — |
| 24 | 73.98 | 7.11 | — | 9.48 | S 9.43 | 74.12 | 7.06 | — | 9.41 | S 9.41 |
| 25 | 78.17 | 7.94 | 6.56 | 7.33 | — | 78.14 | 7.91 | 6.51 | 7.44 | — |
| 26 | 85.04 | 6.49 | 3.94 | 4.53 | — | 84.99 | 6.52 | 3.97 | 4.53 | — |
| 27 | 81.81 | 7.46 | 4.76 | 5.97 | — | 81.91 | 7.85 | 4.78 | 5.46 | — |
| 28 | 83.42 | 6.52 | 4.79 | 5.27 | — | 83.04 | 6.57 | 4.84 | 5.54 | — |
| 29 | 86.79 | 7.93 | — | 5.28 | — | 86.84 | 7.89 | — | 5.26 | — |
| 30 | 88.43 | 7.14 | — | 4.43 | — | 88.52 | 7.10 | — | 4.37 | — |

EXAMPLE 31

A solution was prepared by dissolving 10 g (0.054 mole) of 1-hydroxy-2-acetonaphthone, 8.29 g (0.06 mole) of bicyclo [3.3.1]9-nonylidene and 8 g (0. 113 mole) of pyrrolidine in 300 cc of toluene, and the solution was boiled for 10 hours and water was separated. After termination of the reaction, toluene was removed under reduced pressure, and the remaining chromanone compound was crystallized with acetone. Then, the chromanone compound was dissolved in 200 cc of methanol and sodium boron hydride was gradually added to the solution to form a chromanol compound. Then, 7.47 g of this chromanol compound was heated at 150° to 160° C. together with 4.5 g of anhydrous copper sulfate in a carbon dioxide current for 10 minutes, and the obtained brown viscous liquid was purified by the chromatography on silica gel to obtain 6.9 g of a chromene compound represented by the following formula:

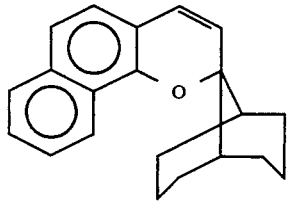

(31)

Figure 2:
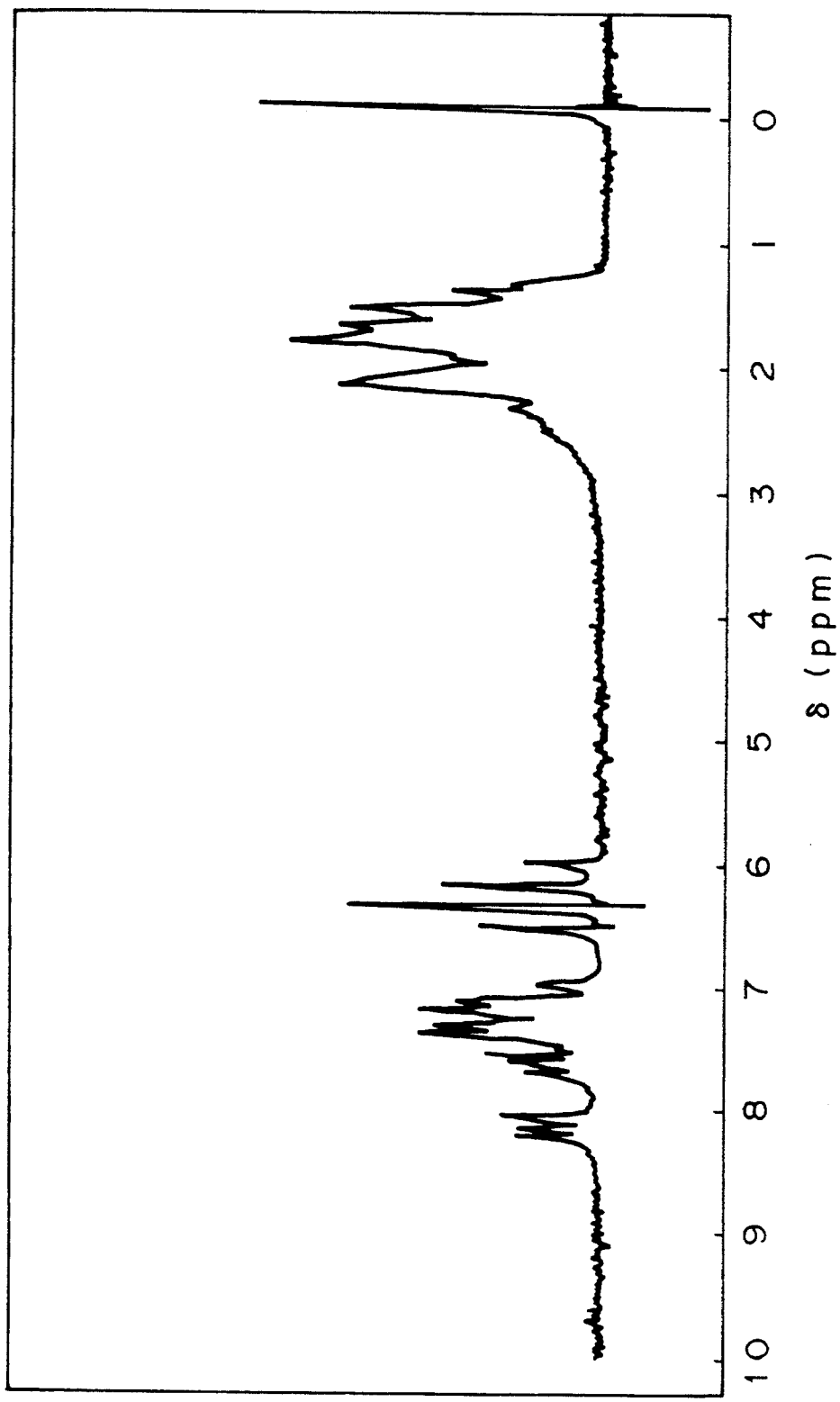
Figure 3:
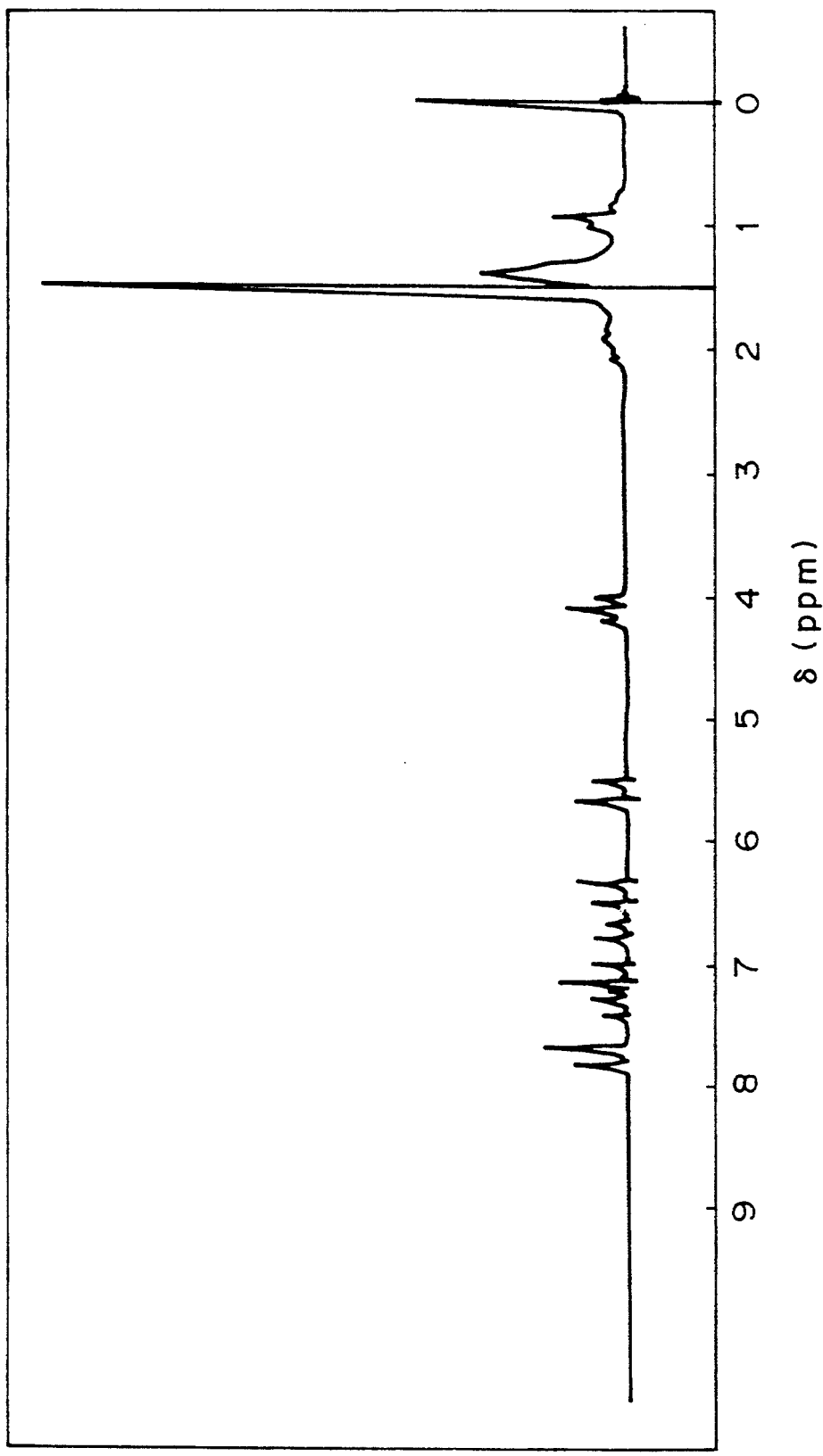

The elementary analysis values of the compound were 86.78% for C, 7.64% for H and 5.58% for O, which were well in agreement with the theoretical values of $C_{21}H_{22}O$, that is, 86.90% for C, 7.59% for H and 5.52% for O. When the proton nucleus magnetic resonance spectrum (FIG. 2) was measured, it was found that a peak of 6H attributed to the proton of the naphthalene ring appeared in the vicinity of $\delta 7.2$ to 8.3 ppm, a peak of 2H attributed to the proton of the alkene appeared in the vicinity of $\delta 5.6$ to 6.7 ppm and a broad peak of 14H attributed to the proton of the bicyclo [3.3.1]9-nonylidene group appeared in the vicinity of $\delta 1.2$ to 2.5 ppm. When the $^{13}C$-nuclear magnetic resonance spectrum was measured, it was found that a peak attributed to the carbon of the bicyclo [3.3.1]9-nonylidene group appeared in the vicinity of $\delta 25$ to 55 ppm, a peak attributed to the carbon of the naphthalene ring appeared in the vicinity of $\delta 110$ to 160 ppm and a peak attributed to the carbon of the alkene appeared in the vicinity of $\delta 80$ to 110 ppm. From the foregoing results, it was confirmed that the isolated product is the compound represented by the above-mentioned structural formula (31).

EXAMPLE 32

A solution was prepared by dissolving 10 g (0.054 mole) of 1-acetyl-2-naphthol, 8.29 g (0.06 mole) of bicyclo [3.3.1]9-nonylidene and 8.7 g (0.10 mole) of morpholine in 300 cc of toluene, and the solution was boiled for 5 hours and water was separated. After termination of the reaction, toluene was removed under reduced pressure and the remaining chromanone compound was recrystallized from acetone. Then, the chromanone compound was dissolved in 200 cc of methanol and lithium aluminum hydride was added to the solution to form a chromanol compound. Then, 6.49 g of this chromanol compound was heated at 170° to 180° C. together with anhydrous copper sulfate in a carbon dioxide current for 10 minutes, and the obtained brown viscous liquid was purified by the chromatography on silica gel to obtain 5.8 g of a chromene compound represented by the following formula:

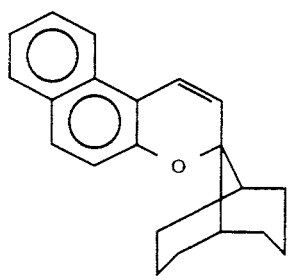

(32)

The elementary analysis values of the obtained compound were 86.81% for C, 7.62% for H and 5.57% for O, which were well in agreement with the theoretical values of $C_{21}H_{22}O$, that is, 86.90% for C, 7.59% for H and 5.52% for O. When the proton nuclear magnetic resonance spectrum was measured, it was found that a peak of 6H attributed to the proton of the naphthalene ring appeared in the vicinity of $\delta7.2$ to 8.3 ppm, a peak of 2H attributed to the proton of the alkene appeared in the vicinity of $\delta6.0$ to 7.0 ppm and a broad peak of 14H attributed to the proton of the bicyclo [3.3.1]9-nonylidene group appeared in the vicinity of $\delta1.2$ to 2.5 ppm. When the $^{13}C$-nuclear magnetic resonance spectrum was measured, it was found that a peak attributed to the carbon of the bicyclo [3.3.1]9-nonylidene group appeared in the vicinity of $\delta27$ to 55 ppm, a peak attributed to the carbon of the naphthalene ring appeared in the vicinity of $\delta110$ to 160 ppm and a peak attributed to the carbon of the alkene appeared in the vicinity of $\delta80$ to 110 ppm. From the foregoing results, it was confirmed that the isolated product is the compound represented by the structural formula (32).

EXAMPLE 33

In 50 cc of anhydrous ether was dissolved 3.06 g. (0.01 mole) of the chromanone compound obtained in Example 32, represented by the following formula:

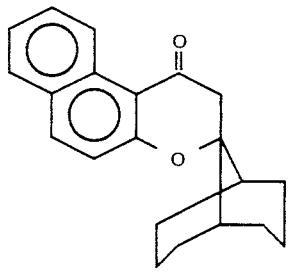

and the solution was cooled to 0° C. and Grignard reagent CH₃MgI (0,012 mole) newly prepared in 50 cc of anhydrous ether was dropped into the solution over a period of about 1 hour. After termination of the dropwise addition, the mixture was stirred at room temperature for 2 hours and quietly poured into cold water to extract the product with ether. The ether extract was dried on magnesium sulfate to form a chromanol compound from the chromanone compound. Then, the chromanol compound was heated at 200° C. together with anhydrous copper sulfate in a carbon dioxide current for about 10 minutes. The obtained brown viscous liquid was purified by the chromatography on silica gel to obtain 2.47 g of a chromene compound represented by the following formula:

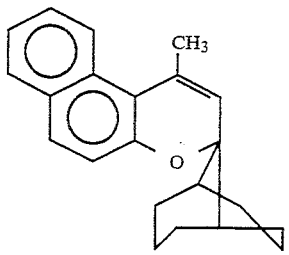

(33)

The elementary analysis, proton nuclear magnetic resonance spectrum measurement and $^{13}C$-nuclear magnetic resonance spectrum measurement were carried out in the same manner as described in Example 32. From the obtained results, it was confirmed that the obtained compound is the compound represented by the above-mentioned structural formula (33). The elementary analysis values of the obtained compound and the theoretical values calculated from the composition of the compound (33) are shown in Table 4.

EXAMPLE 34

In 300 cc of toluene were dissolved 10 g (0.054 mole) of 1-acetyl-2-naphthol, 8.29 g (0.06 mole) of bicyclo [3.3.1]9-nonan-9-one and 8.7 g (0.10 mole) of morpholine, and the solution was boiled for 15 hours and water was separated. After termination of the reaction, toluene was removed under reduced pressure, and the remaining product was recrystallized from acetone to obtain 8.48 g of a compound represented by the following formula:

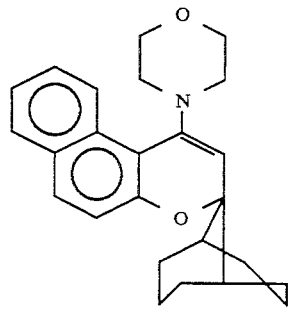

Then, 8.48 g of this compound was dissolved in 100 cc of methanol and reacted with methyl iodide to obtain 7.83 g of a chromanone compound represented by the following formula:

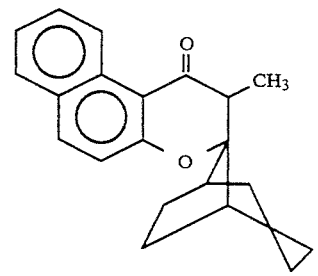

In the same manner as described in Example 32, the formed chromanone compound was converted to a chromanol compound, and the dehydration reaction, separation and purification were carried out to obtain 6.58 g of a chromene compound represented by the following formula:

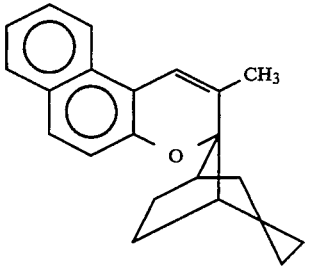

(34)

The elementary analysis, proton nuclear magnetic resonance spectrum measurement and $^{13}$C-nuclear magnetic resonance spectrum measurement were carried out in the same manner as described in Example 32. From the obtained results, it was confirmed that the obtained compound is the compound represented by the above-mentioned structural formula (34). The elementary analysis values of the obtained compound and the theoretical values calculated from the composition of the compound (34) are shown in Table 4.

EXAMPLES 35 THROUGH 60

Various chromene compounds were synthesized from starting compounds shown in Table 3 in the same manner as described in Examples 31 through 34. Namely, in Table 3, in Examples 35 through 39, the reaction was carried out in the same manner as described in Example 34 and in Examples 40 through 55, the reaction was carried out in the same manner as described in Example 31. In Examples 56 through 60, the reaction was carried out in the same manner as described in Example 33 or 34.

The structures of the obtained products were analyzed by the same structure-confirming means as adopted in Example 31. From the obtained results, it was confirmed that the obtained products are compounds represented by the structural formulae shown in Table 3. The elementary analysis values of the obtained compounds and the theoretical values calculated from the structural formulae of the compounds are shown in Table 4.

TABLE 3

| Example No. | Starting Compounds | | Condensing agent | Products | Yield (%) |
|---|---|---|---|---|---|
| 35 | 2-hydroxyacetophenone | cyclooctanone (bicyclic ketone) | pyrrolidine | chromene-bicyclic enamine product | 39 |
| 36 | 2-hydroxy-4-ethyl-6-methoxyacetophenone | cyclooctanone (bicyclic ketone) | morpholine | methoxy-ethyl-chromene morpholine enamine product | 42 |
| 37 | 2-hydroxy-1-naphthylmethylketone | N(CH₃)₂-substituted bicyclic ketone | N-ethyl-N-propylamine (H₅C₂−NH−C₂H₅ with CH group) | naphthochromene-N(CH₃)₂ enamine product | 44 |

TABLE 3-continued

| Example No. | Starting Compounds | Condensing agent | Products | Yield (%) |
|---|---|---|---|---|
| 38 | | | | 39 |
| 39 | | | | 39 |
| 40 | | | | 42 |

TABLE 3-continued
| Example No. | Starting Compounds | | Condensing agent | Products | Yield (%) |
|---|---|---|---|---|---|
| 41 | 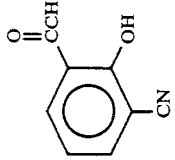 | 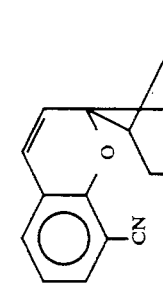 |  | 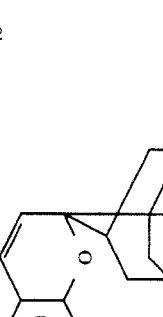 | 38 |
| 42 |  |  | | | 40 |
| 43 | | | | | 31 |

TABLE 3-continued

| Example No. | Starting Compounds | | Condensing agent | Products | Yield (%) |
|---|---|---|---|---|---|
| 44 | (acetyl hydroxyquinoline structure) | (bicyclic ketone) | pyrrolidine | (chromene-quinoline fused product) | 39 |
| 45 | (acetyl hydroxyphenanthrene structure) | (dimethyl bicyclic ketone) | pyrrolidine | (chromene-phenanthrene fused product) | 40 |
| 46 | (acetyl-OH-OC₂H₅-NO₂ benzene) | (trimethyl bicyclic ketone) | " | (chromene with OC₂H₅, NO₂, CH₃ groups) | 31 |
| 47 | (acetyl-OH-C₅H₉-CF₃ benzene) | (trimethyl bicyclic ketone) | pyrrolidine | (chromene with C₅H₉, CF₃, CH₃ groups) | 44 |

TABLE 3-continued
| Example No. | Starting Compounds | Condensing agent | Products | Yield (%) |
|---|---|---|---|---|
| 48 | 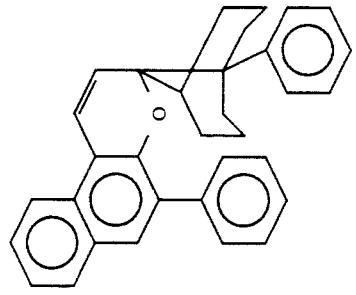 | '' | 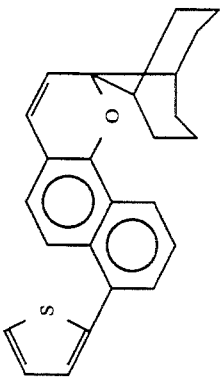 | 41 |
| 49 | 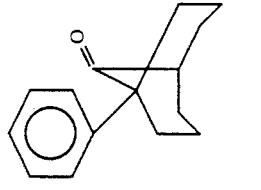 | '' | 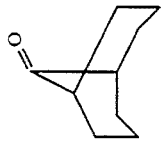 | 40 |
| 50 | 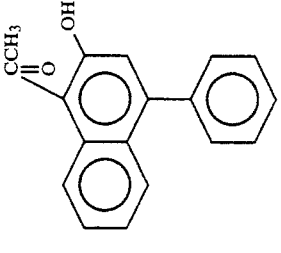 | pyrrolidine | 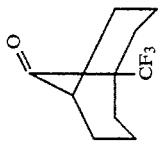 | 38 |

TABLE 3-continued

| Example No. | Starting Compounds | Condensing agent | Products | Yield (%) |
|---|---|---|---|---|
| 51 | (structure: 1-hydroxy-2-acetyl naphthalene with furan substituent) + (bicyclic ketone with CN) | " | (chromene product with furan and CN-bicyclic) | 41 |
| 52 | (structure: 2-acetyl-1,6-dihydroxy-3-bromo naphthalene) + (bicyclic ketone with C4H9 and F) | " | (chromene product with Br, OH, H9C4, F) | 38 |
| 53 | (structure: 1-hydroxy-2-acetyl-6-methoxy-4-dimethylamino naphthalene) + (bicyclic ketone with CH2-phenyl) | pyrrolidine | (chromene product with OCH3, N(CH3)2, CH2-phenyl) | 34 |

TABLE 3-continued

| Example No. | Starting Compounds | Condensing agent | Products | Yield (%) |
|---|---|---|---|---|
| 54 | | | | 36 |
| 55 | | " | | 37 |
| 56 | | CH₂MgBr | | 65 |
| 57 | | CH₂CH₂CH₂CH₂MgBr | | 69 |

TABLE 3-continued

| Example No. | Starting Compounds | Condensing agent | Products | Yield (%) |
|---|---|---|---|---|
| 58 | [pyridine-fused bicyclic ketone structure] | phenyl-MgBr | [4-phenyl pyridine-fused chromene bicyclic structure] | 64 |
| 59 | [naphthalene-fused bicyclic enamine structure with N] | CH₃CH₂CH₂Br | [3-propyl naphtho-chromene bicyclic structure] | 66 |
| 60 | [naphthalene-fused bicyclic enamine structure with N] | PhCH₂CH₂Br | [3-(2-phenylethyl) naphtho-chromene bicyclic structure] | 64 |

TABLE 4

| Compound No. | Elementary Analysis Values (%) | | | | | | | | | | | |
|---|---|---|---|---|---|---|---|---|---|---|---|---|
| | Theoretical Values (%) | | | | | | Found Values (%) | | | | | |
| | C | H | N | O | S | others | C | H | N | O | S | others |
| 31 | 86.90 | 7.59 | — | 5.52 | — | — | 86.78 | 7.64 | — | 5.58 | — | — |
| 32 | 86.90 | 7.59 | — | 5.52 | — | — | 86.81 | 7.62 | — | 5.57 | — | — |
| 33 | 86.80 | 7.95 | — | 5.26 | — | — | 86.77 | 7.96 | — | 5.27 | — | — |
| 34 | 86.80 | 7.95 | — | 5.26 | — | — | 86.79 | 7.98 | — | 5.23 | — | — |
| 35 | 81.51 | 8.80 | 4.53 | 5.17 | — | — | 81.48 | 8.75 | 4.58 | 5.19 | — | — |
| 36 | 75.35 | 8.43 | 3.66 | 12.55 | — | — | 75.38 | 8.39 | 3.68 | 12.55 | — | — |
| 37 | 80.15 | 8.97 | 6.92 | 3.95 | — | — | 80.13 | 8.99 | 6.94 | 3.94 | — | — |
| 38 | 67.93 | 6.39 | 3.17 | 7.24 | 7.25 | Cl 8.02 | 67.88 | 6.42 | 3.15 | 7.19 | 7.22 | Cl 8.14 |
| 39 | 77.08 | 8.02 | 10.79 | 4.11 | — | — | 77.04 | 8.04 | 10.83 | 4.09 | — | — |
| 40 | 80.52 | 8.89 | 4.94 | 5.65 | — | — | 80.49 | 8.92 | 4.96 | 5.63 | — | — |
| 41 | 81.47 | 7.22 | 5.28 | 6.03 | — | — | 81.44 | 7.26 | 5.25 | 6.05 | — | — |
| 42 | 88.19 | 7.90 | — | 3.92 | — | — | 88.22 | 7.88 | — | 3.90 | — | — |
| 43 | 78.73 | 6.61 | — | 4.56 | — | Cl 10.10 | 78.68 | 6.64 | — | 4.53 | — | Cl 10.15 |
| 44 | 82.44 | 7.26 | 4.81 | 5.49 | — | — | 82.42 | 7.28 | 4.83 | 5.47 | — | — |
| 45 | 87.91 | 7.91 | — | 4.18 | — | — | 87.93 | 7.93 | — | 4.14 | — | — |
| 46 | 73.73 | 7.85 | 3.31 | 15.11 | — | — | 73.69 | 7.88 | 3.26 | 15.17 | — | — |
| 47 | 76.29 | 7.73 | — | 3.50 | — | F 12.48 | 76.28 | 7.71 | — | 3.49 | — | F 12.95 |
| 48 | 89.55 | 6.83 | — | 3.62 | — | — | 89.54 | 6.84 | — | 3.62 | — | — |
| 49 | 79.32 | 7.99 | — | 4.22 | 8.47 | — | 79.27 | 8.02 | — | 4.20 | 8.51 | — |
| 50 | 68.88 | 6.50 | 3.35 | 7.64 | — | F 13.63 | 68.84 | 6.47 | 3.33 | 7.67 | — | F 13.69 |
| 51 | 79.97 | 6.72 | 4.05 | 9.26 | — | — | 79.94 | 6.76 | 4.06 | 9.24 | — | — |
| 52 | 63.43 | 5.95 | 2.96 | 6.76 | — | F 4.01 Br 16.88 | 63.37 | 5.97 | 2.98 | 6.74 | — | F 4.03 Br 16.91 |
| 53 | 81.90 | 7.98 | 3.08 | 7.04 | — | — | 81.86 | 7.97 | 3.06 | 7.11 | — | — |
| 54 | 75.58 | 6.89 | — | 8.75 | 8.78 | — | 75.54 | 6.88 | — | 8.77 | 8.81 | — |
| 55 | 77.88 | 9.15 | 6.05 | 6.92 | — | — | 77.90 | 9.17 | 6.03 | 6.90 | — | — |
| 56 | 85.00 | 7.13 | 3.67 | 4.19 | — | — | 85.03 | 7.11 | 3.69 | 4.17 | — | — |
| 57 | 82.20 | 8.46 | 4.36 | 4.98 | — | — | 82.17 | 8.48 | 4.34 | 5.01 | — | — |
| 58 | 83.24 | 7.31 | 4.41 | 5.04 | — | — | 83.17 | 7.33 | 4.43 | 5.07 | — | — |
| 59 | 86.70 | 8.49 | — | 4.81 | — | — | 86.72 | 8.51 | — | 4.77 | — | — |
| 60 | 88.28 | 7.66 | — | 4.06 | — | — | 88.31 | 7.67 | — | 4.02 | — | — |

EXAMPLE 61

The compound synthesized in Example 1, which was represented by the following formula:

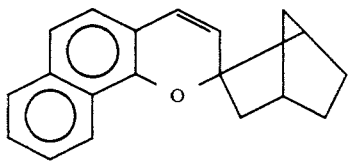

was dissolved and dispersed in polymethyl methacrylate with the aid of benzene, and a cast film was formed on a slide glass sheet (11.2 cm×3.7 cm) so that the concentration of the compound in the film was $1.0 \times 10^{-4}$ mole/g and the thickness of the film was 0.1 mm. The photochromic film was irradiated with rays of mercury lamp (SHL-100 supplied by Toshiba) located 10 cm apart from the film at 25° C.±1° C. for 60 seconds to effect coloration in the film, and the photochromic characteristics were examined with respect to items described below. The obtain results are shown in Table 5.

Maximum absorption wavelength (λmax):

The maximum absorption wavelength λmax of the colored film was determined by using a spectrophotometer (220A supplied by Hitachi).

ε(60 seconds):

After 60 seconds' irradiation under the above-mentioned conditions, the absorbance at the maximum absorption wavelength was measured.

ε(0 second):

The absorbance at the maximum absorption wavelength of the unirradiated film was measured.

Half-value period $t^{\frac{1}{2}}$:

After 60 second's irradiation, the time required for reduction of the absorbance of the film to $\frac{1}{2}$ of [ε(60 seconds)−ε(0 second)] was measured.

EXAMPLE 62 THROUGH 120

The photochromic characteristics of the compounds prepared in Examples 2 through 60 were measured in the same manner as described in Example 61. The obtained results are shown in Table 5. For comparison, films were similarly prepared by using spiroadamantane compounds represented by the following formulae (61) and (62) and the photochromic characteristics were similarly measured:

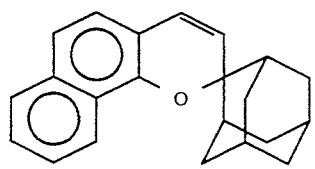

(61)

and

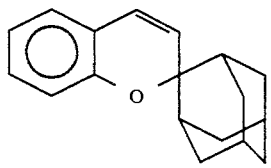

(62)

TABLE 5

| Example No. | Compound No. | Color | ε (60 seconds)− ε (0 seconds) | $\lambda_{max}$ (nm) | $t^{\frac{1}{2}}$ (seconds) |
|---|---|---|---|---|---|
| 61 | 1 | yellow | 0.8 | 448 | 62 |
| 62 | 2 | yellow | 0.6 | 401 | 21 |
| 63 | 3 | yellow | 0.4 | 450 | 15 |
| 64 | 4 | yellow | 0.5 | 450 | 18 |
| 65 | 5 | orange | 0.4 | 480 | 62 |
| 66 | 6 | orange | 0.5 | 480 | 60 |
| 67 | 7 | yellow | 0.7 | 405 | 90 |
| 68 | 8 | yellow | 0.6 | 410 | 70 |
| 69 | 9 | yellow | 1.0 | 440 | 90 |
| 70 | 10 | yellow | 0.8 | 450 | 18 |
| 71 | 11 | orange | 0.6 | 478 | 52 |
| 72 | 12 | yellow | 0.9 | 440 | 60 |
| 73 | 13 | orange | 0.4 | 470 | 53 |
| 74 | 14 | yellow | 0.9 | 436 | 70 |
| 75 | 15 | yellow | 0.8 | 456 | 70 |
| 76 | 16 | red | 0.9 | 490 | 60 |
| 77 | 17 | yellow | 0.9 | 450 | 60 |
| 78 | 18 | orange | 0.9 | 460 | 40 |
| 79 | 19 | red | 0.9 | 490 | 60 |
| 80 | 20 | orange | 0.7 | 470 | 30 |
| 81 | 21 | red | 0.9 | 500 | 55 |
| 82 | 22 | yellow | 0.7 | 430 | 40 |
| 83 | 23 | red | 0.8 | 490 | 50 |
| 84 | 24 | yellow | 0.7 | 450 | 60 |
| 85 | 25 | orange | 0.8 | 470 | 29 |
| 86 | 26 | yellow | 0.3 | 401 | 12 |
| 87 | 27 | orange | 0.2 | 490 | 10 |
| 88 | 28 | orange | 0.3 | 480 | 15 |
| 89 | 29 | yellow | 0.3 | 410 | 10 |
| 90 | 30 | yellow | .03 | 410 | 13 |
| 91 | 31 | yellow | 1.0 | 448 | 120 |
| 92 | 32 | yellow | 0.8 | 400 | 60 |
| 93 | 33 | yellow | 0.6 | 450 | 40 |
| 94 | 34 | yellow | 0.7 | 450 | 40 |
| 95 | 35 | orange | 0.6 | 480 | 120 |
| 96 | 36 | orange | 0.7 | 480 | 120 |
| 97 | 37 | yellow | 0.9 | 405 | 180 |
| 98 | 38 | yellow | 0.8 | 410 | 135 |
| 99 | 39 | yellow | 1.2 | 440 | 175 |
| 100 | 40 | yellow | 0.9 | 450 | 39 |
| 101 | 41 | orange | 0.7 | 478 | 106 |
| 102 | 42 | yellow | 1.0 | 440 | 118 |
| 103 | 43 | orange | 0.6 | 470 | 113 |
| 104 | 44 | yellow | 1.0 | 436 | 140 |
| 105 | 45 | yellow | 1.0 | 456 | 135 |
| 106 | 46 | red | 1.1 | 490 | 120 |
| 107 | 47 | yellow | 1.0 | 450 | 116 |
| 108 | 48 | orange | 1.0 | 460 | 82 |
| 109 | 49 | red | 1.1 | 490 | 120 |
| 110 | 50 | orange | 0.9 | 470 | 60 |
| 111 | 51 | red | 1.0 | 500 | 110 |
| 112 | 52 | yellow | 0.9 | 430 | 78 |
| 113 | 53 | red | 1.0 | 490 | 106 |
| 114 | 54 | yellow | 0.8 | 450 | 119 |
| 115 | 55 | orange | 1.0 | 470 | 59 |
| 116 | 56 | yellow | 0.5 | 400 | 26 |
| 117 | 57 | orange | 0.4 | 490 | 19 |
| 118 | 58 | orange | 0.5 | 480 | 32 |
| 119 | 59 | yellow | 0.5 | 410 | 20 |
| 120 | 60 | yellow | 0.5 | 410 | 28 |
| Comparative Example No. | | | | | |
| 1 | 61 | yellow | 0.9 | 448 | 240 |
| 2 | 62 | not colored | — | — | — |

EXAMPLE 121

A solution was prepared by dissolving 10 g (0.0318 mole) of 5-n-octyloxy-1-hydroxy-2-acetonaphthone, 2.77 g (0.0477 mole) of acetone and 1.13 g (0.0159 mole) of pyrrolidine 100 ml of toluene, and the solution was boiled for 10 hours and water was separated. After termination of the reaction, toluene was removed under reduced pressure, and the remaining chromanone compound was dissolved in 100 ml of methanol and sodium boron hydride was gradually added to the solution to form a chromanol compound. Then, 6.0 g of the chromanol compound was heated at 150° to 160° C. together with 4.0 g of anhydrous copper sulfate in a carbon dioxide current for 10 minutes. The obtained brown viscous liquid was purified by the chromatography on silica gel to obtain 3.8 g of a chromene compound represented by the following formula:

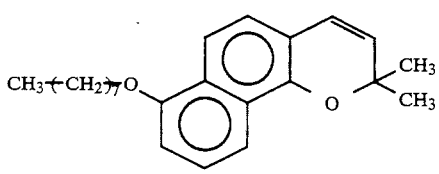

(121)

The elementary analysis values of the obtained compound were 81.58% for C, 9.01% for H and 9.41% for O, which were well in agreement with the theoretical values of $C_{23}H_{30}O_2$, that is, 81.61% for C, 8.93% for H and 9.46% for O. When the proton nuclear magnetic resonance spectrum was measured, it was found that a broad peak of 15H attributed to the proton of the n-octyloxy group appeared in the vicinity of δ0.6 to 2.3 ppm, a peak of 6H attributed to the proton of the methyl group bonded to the 2-position of the chromene appeared in the vicinity of δ1.5 ppm, a triplet peak attributed to the proton of the methylene bonded to the oxygen of the n-octyloxy group appeared in the vicinity of δ4 ppm, doublet peaks of the protons bonded to the 3- and 4-positions of the chromene appeared in the vicinity of δ5.6 ppm and in the vicinity of δ6.4 ppm, respectively, and a peak of 5H attributed to the proton of the naphthalene ring appeared in the vicinity of δ6.5 to 8.0 ppm. When the $^{13}$C-NMR was measured, it was found that a peak attributed to the carbon of the methyl group bonded to the 2-position and a peak attributed to the carbon of the octyloxy group appeared in the vicinity of 14 to 40 ppm, a peak attributed to the carbon bonded to the oxygen of the octyloxy group appeared in the vicinity of δ70 ppm, a peak attributed to the carbon at the 2-position of the chromene appeared in the vicinity of δ80 ppm, a peak attributed to the carbon at the 3,4-position of the chromene and a peak attributed to the carbon on the naphthalene ring appeared in the vicinity of δ115 to 135 ppm, and a peak attributed to the carbon on the naphthalene ring, bonded to the oxygen, appeared in the vicinity of δ150 ppm. From the foregoing results, it was confirmed that the isolated product is the compound represented by the above-mentioned structural formula (121).

EXAMPLE 122

In 100 ml of toluene was dissolved 10 g (0.0328 mole) of a compound represented by the following formula:

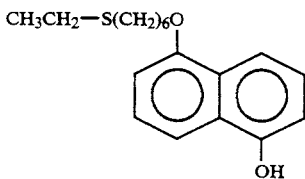

and 18.71 g (0.00820 mole) of titanium tetraethoxide was added to the solution at room temperature. Ethanol was removed by azeotropic distillation. Then, toluene was added to the residue to form 500 ml of a reaction liquid. Then, a solution of 4.14 g (0.0492 mole) of 3-methyl-2-butenal in 300 m of toluene was added to the reaction liquid and the mixture was refluxed for 8 hours. After the reaction, a saturated aqueous solution of ammonium chloride was added to the reaction liquid and the mixture was extracted with ether. The solvent was removed under reduced pressure and the remaining product was purified by the chromatography on silica gel to obtain 6 g of a chromene compound represented by the following formula:

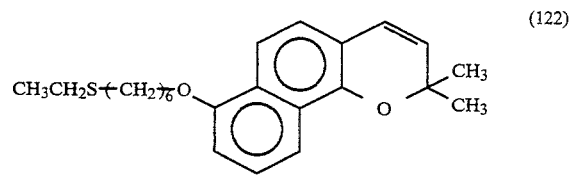

(122)

The elementary analysis values of the obtained compound were 74.61% for C, 8.03% for H, 8.64% for S and 8.72% for O, which were well in agreement with the theoretical values calculated from $C_{23}H_{30}O_2S$, that is, 74.55% for C, 8.16% for H, 8.65% for S and 8.64% for O. When the proton nuclear magnetic resonance spectrum was measured, it was found that a broad peak of 8H attributed to the methylene bonded to the carbon appeared in the vicinity of δ1.0 to 2.3 ppm, a triplet peak attributed to the methyl of the ethyl group bonded to the sulfur atom appeared in the vicinity of δ1.3 ppm, a multiplet peak of 4H attributed to the proton of the methylene bonded to the sulfur appeared in the vicinity of δ2.5 ppm, a triplet peak of 2H attributed to the proton of the methylene bonded to the oxygen appeared in the vicinity of δ4 ppm, doublet peaks attributed to the protons bonded to the 3- and 4-positions of the chromene appeared in the vicinity of δ5.6 ppm and in the vicinity of δ6.4 ppm, respectively, and a peak of 5H attributed to the proton of the naphthalene ring appeared in the vicinity of g 6.5 to 8.0 ppm. When the $^{13}$C-NMR was measured, it was found that a peak attributed to the carbon of the methyl group bonded at the 2-position and a peak attributed to the long-chain alkylene group appeared in the vicinity of δ14 to 40 ppm, a peak attributed to the carbon of the methylene bonded to the oxygen appeared in the vicinity of δ70 ppm, a peak attributed to the carbon at the 2-position of the chromene appeared in the vicinity of δ80 ppm, a peak attributed to the carbon at the 3,4-position of the chromene and a peak attributed to the carbon of the naphthalene ring appeared in the vicinity of δ115 to 135 ppm, and a peak attributed to the carbon of the naphthalene ring bonded to the oxygen appeared in the vicinity of δ150 ppm.

From the foregoing results, it was confirmed that the isolated product is the compound represented by the above-mentioned structural formula (122).

EXAMPLE 123 THROUGH 146

Various chromene compounds were synthesized from starting compounds show in Table 6 in the same manner as described in Examples 121 and 122.

The structures of the obtained compounds were analyzed by using the same structure-confirming means as adopted in Example 121. It was confirmed that the obtained compounds are compounds represented by structural formulae shown in Table 6. The elementary analysis values of the obtained compounds and the theoretical values calculated from the structural formulae of the compounds are shown in Table 7.

TABLE 6

| Example No. | Starting Compounds | Condensing agent | Products | Yield (%) |
|---|---|---|---|---|
| 123 | naphthalene with O-(CH₂)₁₀-CH₃, OH, and H₃CC(=O) substituents | morpholine | chromene-fused naphthalene with CH₃-(CH₂)₁₀-O substituent and gem-dimethyl | 42 |
| 124 | naphthalene with CH₂-(CH₂)₆-CH₃, OH, and H₃CC(=O) substituents | piperidine | chromene-fused naphthalene with CH₃-(CH₂)₇ substituent and gem-dimethyl | 45 |
| 125 | naphthalene with (CH₂)₁₀-CH₃, OH, and H₃CC(=O) substituents | HN(C₂H₅)₂ | chromene-fused naphthalene with CH₃-(CH₂)₁₉ substituent and gem-dimethyl | 37 |
| 126 | quinoline with (CH₂)₇SCH₃, OH, and H₃CC(=O) substituents | pyrrolidine | chromene-fused quinoline with CH₂-(CH₂)₆SCH₃ substituent and gem-dimethyl | 43 |
| 127 | naphthalene with CH₃, CH₂-(CH₂)₇-N(C₂H₅)₂, OH, and H₃CC(=O) substituents | pyrrolidine | chromene-fused naphthalene with H₃C and (CH₃CH₂)₂N-(CH₂)₇-N-CH₂ substituents and gem-dimethyl | 40 |

TABLE 6-continued

| Example No. | Starting Compounds | | Condensing agent | Products | Yield (%) |
| --- | --- | --- | --- | --- | --- |
| 128 | 4-(O-(CH₂)₇CH₃)-1-hydroxy-2-acetylnaphthalene | CH₃CCH₃ (O=) | pyrrolidine (NH) | chromene-naphthalene with CH₃(CH₂)₇O- and gem-dimethyl | 48 |
| 129 | naphthalenediol with CH₂=CH(CH₂)₁₀CH₃ and CH₂(CH₂)₃SCH₂CH₃ | CH₃C(CH₃)=CHCHO | Ti(OC₂H₅)₄ | chromene with CH₃(CH₂)₁₁ and (CH₂)₆SCH₂CH₃ | 60 |
| 130 | hydroxynaphthalene with O-(CH₂)₆OP(OCH₂CH₂CH₃)₂ | CH₃C(CH₃)=CHCHO | Ti(OC₂H₅)₄ | chromene-naphthalene with (CH₃CH₂CH₂O)₂PO(CH₂)₆O- | 65 |
| 131 | naphthalenediol with (CH₂)₇CH₃ and CH₂(CH₂)₆CH₃ | CH₃C(CH₃)=CHCHO | CH₃CH₂MgBr | chromene-naphthalene with CH₃(CH₂)₇ and CH₂(CH₂)₆CH₃ | 70 |
| 132 | benzothiophene with OH and CH₂(CH₂)₃CH₃ | CH₃C(CH₃)=CHCHO | Al(OEt)₃ | chromene fused benzothiophene with CH₃(CH₂)₅ | 50 |

TABLE 6-continued

| Example No. | Starting Compounds | Condensing agent | Products | Yield (%) |
|---|---|---|---|---|
| 133 | [structure: hydroxyquinoline with CH₂(CH₂)₅S—CH₂CH₃ substituent] | CH₃C(CH₃)=CHCHO | SnCl₄ | [chromene fused quinoline structure] CH₃CH₂—S(CH₂)₆ | 40 |
| 134 | [structure: benzofuran with OH and (CH₂)₆N(C₂H₅)₂] | CH₃C(CH₃)=CHCHO | SnCl₄ | [chromene-benzofuran structure] (CH₃CH₂)₂N(CH₂)₆ | 35 |
| 135 | [naphthalene with OH and O(CH₂)₇P(CH₂CH₃)₂] | CH₃C(CH₃)=CHCHO | Ti(OCH₂CH₂CH₂CH₃)₄ | [chromene-naphthalene structure] (CH₃CH₂)₂P(CH₂)₇O | 68 |
| 136 | [naphthalene with OH and O(CH₂)₇P(OCH₂CH₃)₂] | " | Ti(OCH₂CH₂CH₂CH₃)₄ | [chromene-naphthalene] O(CH₂)₇P(OCH₂CH₃)₂ | 70 |
| 137 | [naphthalene with CH₂(CH₂)₅OP(OCH₂CH₃)₂, OH, and CH₂CH₂SCH₂CH₃] | " | Ti{OCH(CH₃)CH₃}₄ | [chromene-naphthalene with CH₂CH₂SCH₂CH₂ and (CH₃CH₂O)₂PO(CH₂)₆] | 52 |

TABLE 6-continued

| Example No. | Starting Compounds | Condensing agent | Products | Yield (%) |
|---|---|---|---|---|
| 138 | 4,8-dimethyl-1-naphthol with CH₂(CH₂)₆CH₃ substituent | Ti(OCH₂CH₃)₄ | 2,2-dimethyl-chromene fused naphthalene with CH₃(CH₂)₇ and two CH₃ groups | 75 |
| 139 | 5-chloro-naphthol with CH₂(CH₂)₉SCH₂CH₃ substituent; CH₃C(CH₃)=CHCHO | Al(OCH₂CH₃)₃ | chromene-naphthalene with Cl and CH₃CH₂S(CH₂)₁₀ | 55 |
| 140 | quinolinol with CH₂(CH₂)₇SCH₂CH₃ | " | chromene-quinoline with (CH₂)₈S—CH₂CH₃ | 60 |
| 141 | naphthol with CH₂(CH₂)₉OPO(OCH₂CH₃)(CH₂)₇SCH₂CH₃ substituent | Ti(OCH₂CH₃)₄ | chromene-naphthalene with CH₃CH₂OPO(OCH₂)₇CH₃/(CH₂)₁₀ | 50 |
| 142 | naphthol with (CH₂)₁₂N(CH₃)CH₂CH₃ | " | chromene-naphthalene with CH₃CH₂—N(CH₃)—(CH₂)₁₂ | 45 |

TABLE 6-continued
| Example No. | Starting Compounds | Condensing agent | Products | Yield (%) |
|---|---|---|---|---|
| 143 | 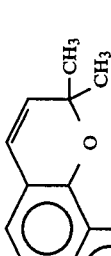 | CH₃C(CH₃)=CHCHO  Ti(OCH₂CH₃)₄ | 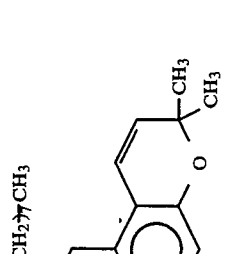 | 63 |
| 144 | 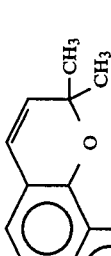 | " | 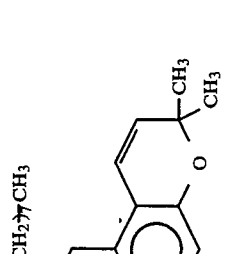 | 67 |
| 145 | 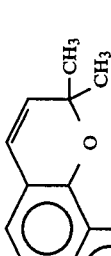 | " | 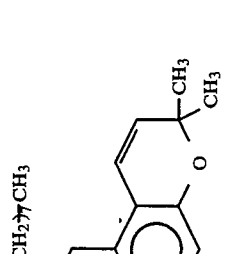 | 72 |
| 146 | 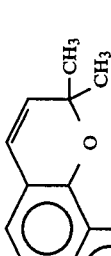 | " | 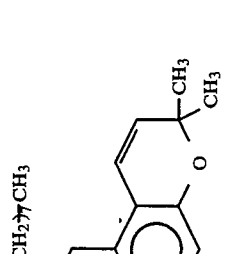 | 60 |

TABLE 7

| Compound No. | Analysis Values (%) C | H | N | O | others | | Theoretical Values (%) C | H | N | O | others | |
|---|---|---|---|---|---|---|---|---|---|---|---|---|
| 123 | 84.36 | 6.99 | — | 8.65 | — | | 84.29 | 7.07 | — | 8.64 | — | |
| 124 | 85.05 | 9.81 | — | 5.14 | — | | 85.11 | 9.74 | — | 5.15 | — | |
| 125 | 85.48 | 11.21 | — | 3.31 | — | | 85.65 | 11.09 | — | 3.26 | — | |
| 126 | 74.30 | 8.27 | 3.90 | 4.51 | S: | 9.08 | 74.32 | 8.22 | 3.94 | 4.50 | S: | 9.02 |
| 127 | 82.37 | 10.36 | 3.52 | 3.75 | — | | 82.50 | 10.14 | 3.44 | 3.92 | — | |
| 128 | 81.46 | 8.71 | — | 9.83 | — | | 81.61 | 8.93 | — | 9.46 | — | |
| 129 | 80.31 | 10.62 | — | 3.09 | S: | 5.98 | 80.40 | 10.41 | — | 3.06 | S: | 6.13 |
| 130 | 68.51 | 8.12 | — | 16.96 | P: | 6.41 | 68.33 | 8.28 | — | 16.86 | P: | 6.53 |
| 131 | 85.73 | 10.41 | — | 3.86 | — | | 85.65 | 10.67 | — | 3.68 | — | |
| 132 | 77.61 | 7.31 | — | 5.15 | S: | 9.93 | 77.73 | 7.46 | — | 4.93 | S: | 9.88 |
| 133 | 74.17 | 8.30 | 3.86 | 4.60 | S: | 9.07 | 74.32 | 8.22 | 3.94 | 4.50 | S: | 9.02 |
| 134 | 77.49 | 9.50 | 3.87 | 9.14 | — | | 77.70 | 9.36 | 3.94 | 9.00 | — | |
| 135 | 75.41 | 8.86 | — | 8.03 | P: | 7.70 | 75.35 | 8.85 | — | 8.03 | P: | 7.77 |
| 136 | 70.23 | 8.40 | — | 14.57 | P: | 6.80 | 70.25 | 8.39 | — | 14.39 | P: | 6.97 |
| 137 | 67.21 | 8.34 | — | 12.40 | S: P: | 6.07 5.98 | 67.15 | 8.36 | — | 12.34 | S: P: | 6.18 5.97 |
| 138 | 85.52 | 9.81 | — | 4.67 | — | | 85.66 | 9.78 | — | 4.56 | — | |
| 139 | 72.77 | 8.46 | — | 3.62 | S: Cl: | 7.30 7.85 | 72.86 | 8.38 | — | 3.59 | S: Cl: | 7.20 7.97 |
| 140 | 75.26 | 8.57 | 3.58 | 4.18 | S: | 8.41 | 75.15 | 8.67 | 3.65 | 4.17 | S: | 8.36 |
| 141 | 71.76 | 9.75 | — | 12.31 | P: | 6.18 | 71.88 | 9.80 | — | 12.34 | P: | 5.98 |
| 142 | 82.01 | 10.97 | 3.27 | 3.75 | — | | 82.09 | 11.07 | 3.19 | 3.65 | — | |
| 143 | 77.21 | 9.42 | — | 6.69 | S: | 6.68 | 77.13 | 9.60 | — | 6.63 | S: | 6.64 |
| 144 | 81.63 | 9.21 | — | 9.16 | — | | 81.77 | 9.15 | — | 9.08 | — | |
| 145 | 85.70 | 10.79 | — | 3.51 | — | | 85.65 | 10.67 | — | 3.68 | — | |
| 146 | 66.60 | 7.49 | — | 18.58 | S: | 7.33 | 66.67 | 7.41 | — | 18.51 | S: | 7.41 |

EXAMPLE 147

The compound synthesized in Example 121, which was represented by the following formula:

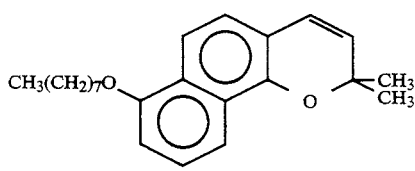

was dissolved and dispersed in polymethyl methacrylate with the aid of benzene, and a cast film was formed on a slide glass sheet (11.2cm×3.7 cm) so that the concentration of the compound in the film was $1.0 \times 10^{-4}$ mole/g and the thickness of the film was 0.1 mm. The photochromic film was irradiated with rays of a mercury lamp (SILL-100 supplied by Toshiba) located 10 cm apart from the film at 25° C.±1° C. for 60 seconds to effect coloration in the film, and the photochromic characteristics were examined with respect to items described below. The obtained results are shown in Table 8.

Maximum absorption wavelength (λmax):

The maximum absorption wavelength λmax of the colored film was determined by using a spectrophotometer (220A supplied by Hitachi).

ε(60 seconds):

After 60 seconds' irradiation under the above-mentioned conditions, the absorbance at the maximum absorption wavelength was measured.

ε(0 second):

The absorbance at the maximum absorption wavelength of the unirradiated film was measured.

Half-value period $t^{\frac{1}{2}}$:

After 60 seconds' irradiation, the time required for reduction of the absorbance of the film to ½ of [ε(60seconds)−ε(0 second)] was measured.

Life $T^{\frac{1}{2}}$:

The photochromic film was irradiated by Xenon Long-Life Fade Meter FAL-250 AX-HC supplied by Suga Shikenki, and the time required for the color density to decrease to ½ of the initial value measured.

EXAMPLES 148 THROUGH 172

The photochromic characteristics of the compounds prepared in Examples 122 through 146 were measured in the same manner as described in Example 147. The obtained results are shown in Table 8. For comparison, films were similarly prepared by using chromene compounds represented by the following formulae (173) through (175) and the photochromic characteristics were similarly measured:

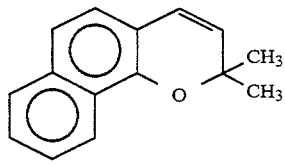
(173)

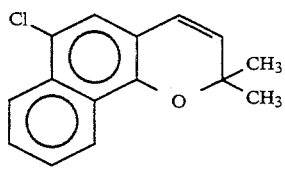
(174)

and

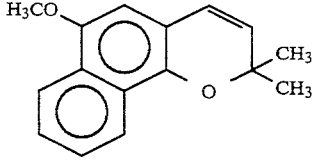
(175)

TABLE 8

| Example No. | Compound No. | $\lambda_{max}$ (nm) | $\epsilon$ (60 seconds)–$\epsilon$(0 seconds) | $t^{\frac{1}{2}}$ (seconds) | $T^{\frac{1}{2}}$ (hours) |
| --- | --- | --- | --- | --- | --- |
| 147 | 121 | 466 | 0.6 | 60 | 70 |
| 148 | 122 | 466 | 0.6 | 40 | 65 |
| 149 | 123 | 466 | 0.6 | 59 | 70 |
| 150 | 124 | 450 | 0.5 | 58 | 80 |
| 151 | 125 | 450 | 0.6 | 58 | 80 |
| 152 | 126 | 445 | 0.7 | 42 | 90 |
| 153 | 127 | 450 | 0.5 | 35 | 80 |
| 154 | 128 | 468 | 0.5 | 70 | 70 |
| 155 | 129 | 452 | 0.6 | 35 | 80 |
| 156 | 130 | 466 | 0.5 | 28 | 70 |
| 157 | 131 | 452 | 0.6 | 57 | 90 |
| 158 | 132 | 489 | 0.5 | 65 | 80 |
| 159 | 133 | 450 | 0.6 | 42 | 75 |
| 160 | 134 | 430 | 0.5 | 46 | 70 |
| 161 | 135 | 446 | 0.6 | 46 | 80 |
| 162 | 136 | 440 | 0.1 | 18 | 50 |
| 163 | 137 | 450 | 0.5 | 25 | 70 |
| 164 | 138 | 457 | 0.5 | 60 | 80 |
| 165 | 139 | 450 | 0.6 | 41 | 85 |
| 166 | 140 | 440 | 0.6 | 40 | 90 |
| 167 | 141 | 450 | 0.5 | 30 | 75 |
| 168 | 142 | 450 | 0.5 | 38 | 80 |
| 169 | 143 | 467 | 0.5 | 42 | 85 |
| 170 | 144 | 412 | 0.1 | 17 | 70 |
| 171 | 145 | 452 | 0.6 | 57 | 85 |
| 172 | 146 | 445 | 0.6 | 39 | 80 |
| Comparative Example No. 1 | 173 | 445 | 0.5 | 80 | 20 |
| Comparative Example No. 2 | 174 | 464 | 0.5 | 90 | 15 |
| Comparative Example No. 3 | 175 | 466 | 0.5 | 90 | 25 |

We claim:

1. A photochromic compound represented by the following general formula (II):

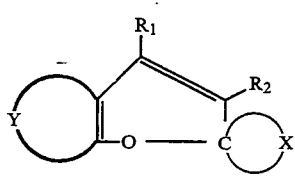

wherein $R_1$ and $R_2$, which may be the same or different, represent a hydrogen atom, an alkyl group having 1 to 20 carbon atoms, a phenyl group, a benzyl group, a phenethyl group, an alkylamino group having 1 to 4 carbon atoms, or a dialkylamino group having 2 to 8 carbon atoms,

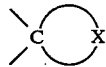

represents a norbornylidene group or a bicyclo [3.3.1]9-nonylidene group which may be substituted with at least one member selected from the group consisting of a halogen atom, a cyano group, an alkyl group having 1 to 4 carbon atoms, an alkoxy group having 1 to 4 carbon atoms, a halogenoalkyl group having 1 to 4 carbon atoms, a phenyl group, a benzyl group, and a dialkylamino group having 2 to 8 carbon atoms, a phenyl group, a benzyl group and a dialkylamino group having 2 to 8 carbon atoms;

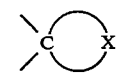

represents a divalent unsaturated heterocyclic group selected from the group consisting of a pyridine ring, and a quinoline ring, which may be substituted with at least one member selected from the group consisting of a halogen atom, a hydroxyl group, a cyano group, a nitro group, an alkyl group having 1 to 20 carbon atoms, an alkoxy group having 1 to 20 carbon atoms, a phenyl group, an alkylamino group having 1 to 4 carbon atoms, a dialkylamino group having 2 to 8 carbon atoms, and a halogenalkyl group having 1 to 4 carbon atoms.

2. A compound as set forth in claim 1, wherein

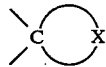

represents said norbornylidene group or said bicyclo [3.3.1]9-nonylidene group which may be substituted with 1 to 3 members which can be the same or different, and are selected from the group consisting of a halogen atom, a cyano group, an alkyl group having 1 to 4 carbon atoms, an alkoxy group having 1 to 4 carbon atoms, a halogenoalkyl group having 1 to 4 carbon atoms, a phenyl group, a benzyl group, and a dialkylamino group having 2 to 8 carbon atoms.

3. A compound as set forth in claim 1, wherein

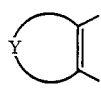

represents a divalent unsaturated heterocyclic group selected from the group consisting of a pyridine ring, and a quinoline ring, which may be substituted with up to five members which may be the same or different selected from the group consisting of a halogen atom, a hydroxyl group, a cyano group, a nitro group, an alkyl group having 1 to 20 carbon atoms, an alkoxy group having 1 to 20 carbon atoms, a phenyl group, an alkylamino group having 1 to 4 carbon atoms, a dialkylamino group having 2 to 8 carbon atoms, and a halogenalkyl group having 1 to 4 carbon atoms.

4. A compound as set forth in claim 1, wherein

represents a divalent unsaturated heterocyclic group selected from the group consisting of a pyridine ring, and a quinoline ring, which may be substituted with 1 to 3 members which may be the same or different selected from the group consisting of a halogen atom, a hydroxyl group, a cyano group, a nitro group, an alkyl group having 1 to 20 carbon atoms, an alkoxy group having 1 to 20 carbon atoms, a phenyl group, an alkylamino group having 1 to 4 carbon atoms, a dialkylamino group having 2 to 8 carbon atoms, and a halogenalkyl group having 1 to 4 carbon atoms.

5. A compound as set forth in claim 1 selected from the group consisting of

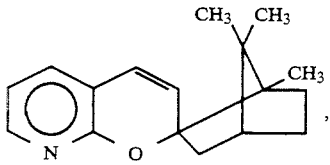
(9)

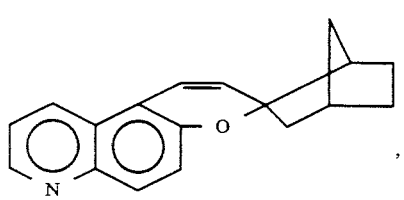
(14)

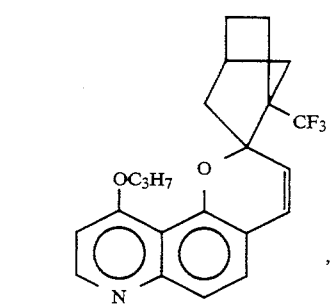
(20)

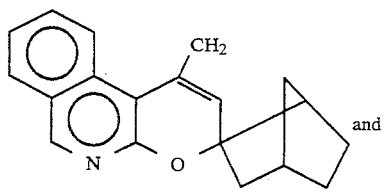
(26)

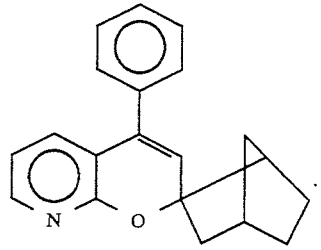
(28)

6. A compound as set forth in claim 1 selected from the group consisting of:

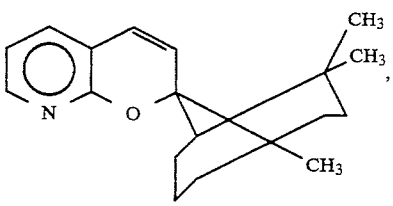
(40)

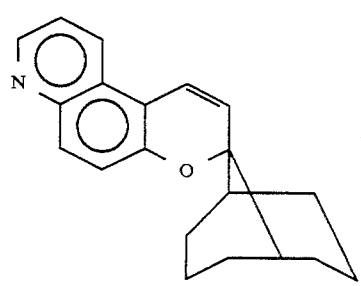
(44)

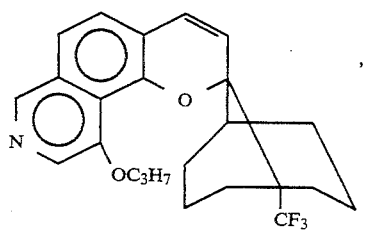
(50)

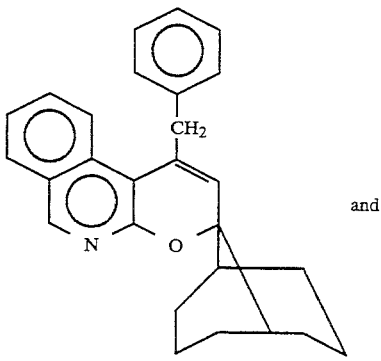
(56)

7. A compound as set forth in claim 1, wherein

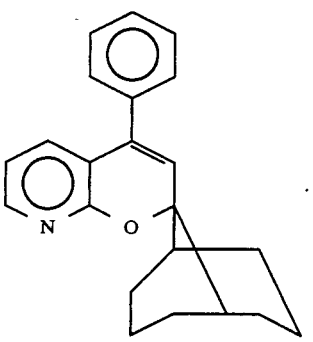

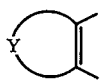

represents a quinoline ring which may be substituted with at least one member selected from the group consisting of a halogen atom, a hydroxyl group, a cyano group, a nitro group, an alkyl group having 1 to 20 carbon atoms, an alkoxy group having 1 to 20 carbon atoms, a phenyl group, an alkylamino group having 1 to 4 carbon atoms, a dialkylamino group having 2 to 8 carbon atoms, and a halogenalkyl group having 1 to 4 carbon atoms.

8. A compound as set forth in claim 3, wherein

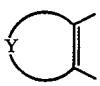

represents a quinoline ring which may be substituted with up to five members which may be the same or different selected from the group consisting of a halogen atom, a hydroxyl group, a cyano group, a nitro group, an alkyl group having 1 to 20 carbon atoms, an alkoxy group having 1 to 20 carbon atoms, a phenyl group, an alkylamino group having 1 to 4 carbon atoms, a dialkylamino group having 2 to 8 carbon atoms, and a halogenalkyl group having 1 to 4 carbon atoms.

9. A compound as set forth in claim 4, wherein

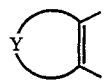

represents a quinoline ring which may be substituted with 1 to 3 members which may be the same or different selected from the group consisting of a halogen atom, a hydroxyl group, a cyano group, a nitro group, an alkyl group having 1 to 20 carbon atoms, an alkoxy group having 1 to 20 carbon atoms, a phenyl group, an alkylamino group having 1 to 4 carbon atoms, a dialkylamino group having 2 to 8 carbon atoms, and a halogenalkyl group having 1 to 4 carbon atoms.

10. A compound according to claim 7 wherein the quinoline ring has one of the following structures:

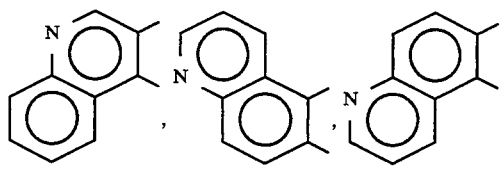

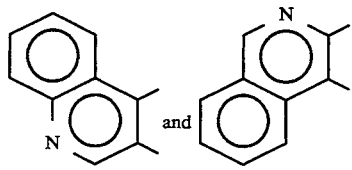

* * * * *